United States Patent

Tsaklakidis et al.

[11] Patent Number: 5,972,947
[45] Date of Patent: Oct. 26, 1999

[54] OXAZOLIDINONE DERIVATIVES, PROCESSES FOR THE PRODUCTION THEREOF AND PHARMACEUTICAL AGENTS CONTAINING THESE COMPOUNDS

[75] Inventors: Christos Tsaklakidis, Weinheim; Wolfgang Schäfer, Mannheim; Liesel Dörge, Mannheim; Walter-Gunar Friebe, Mannheim; Angelika Esswein, Singen, all of Germany

[73] Assignee: Roche Diagnostics GmbH, Mannehim, Germany

[21] Appl. No.: 09/224,799

[22] Filed: Dec. 31, 1998

Related U.S. Application Data

[63] Continuation of application No. 08/973,877, filed as application No. PCT/EP96/02939, Jul. 4, 1996, abandoned.

[30] Foreign Application Priority Data

Jul. 7, 1995 [DE] Germany ........................ 195 24 765 .5

[51] Int. Cl.[6] ...................... A61K 31/505; A61K 31/445; C07D 413/04; C07D 413/14
[52] U.S. Cl. .......................... 514/256; 514/275; 514/316; 514/318; 514/252; 544/238; 544/324; 544/333; 544/365; 546/187; 546/193; 546/194

[58] Field of Search ...................... 546/187, 193, 546/194; 544/324, 333, 238, 365; 514/256, 275, 316, 318, 252

[56] References Cited

U.S. PATENT DOCUMENTS

| 5,532,255 | 7/1996 | Raddatz | .................................. 514/326 |
| 5,556,977 | 9/1996 | Wayne | .................................. 544/360 |

*Primary Examiner*—Evelyn Mei Huang
*Attorney, Agent, or Firm*—Nikaido Marmelstein Murray & Oram LLP

[57] ABSTRACT

The present invention concerns new oxazolidinone derivatives, processes for their production as well as pharmaceutical agents containing these substances. The present invention concerns compounds of the general formula I

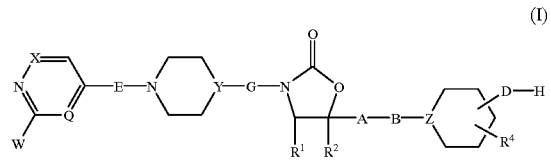

in which the symbols have the meanings as listed in the claims.

11 Claims, No Drawings

OXAZOLIDINONE DERIVATIVES, PROCESSES FOR THE PRODUCTION THEREOF AND PHARMACEUTICAL AGENTS CONTAINING THESE COMPOUNDS

This application is a continuation of Ser. No. 08/973,877 filed Jan. 1, 1998, abandoned, which is the national phase of PCT/EP96102939, filed Jul. 4, 1996 published as WO 97/03072 on Jan. 30, 1997.

It is known that compounds which carry a basic and an acidic group are capable of inhibiting the aggregation of blood platelets when there is a certain distance between the basic and acidic group in the compounds (Drugs of the Future 19(2):135–159 (1994). Compounds with anti-aggregatory action on blood platelets have been described in the patent specifications WO 93/14077, EP-A-O 537/980, EP-A-O 542 363, WO 94/22834, WO 94/22835 and EP 0623615A1.

The present invention concerns new oxazolidinone derivatives, processes for the production thereof as well as pharmaceutical agents containing these substances.

It has now been found that oxazolidinone derivatives effectively inhibit the aggregation of blood platelets and thus can be used to treat diseases which are due to thromboembolic occurrences such as stroke, myocardial infarction or arterial occlusion diseases as well as inflammations, osteoporosis or tumour diseases.

The present invention concerns compounds of the general formula I,

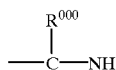

(I)

in which

X, Y and Q independently of one another denote nitrogen or CH

W denotes hydrogen or $NR^{O}R^{OO}$

Z denotes nitrogen, CH or C—OH

A, E and G independently of one another denote a valency dash or an alkylene chain —$(CH_2)_n$ B denotes a valency dash and also denotes a carbonyl group in the case that Z equals N D denotes a side chain in the form of —$(CHR^3)_m$—COO— or =$CR^3$—COO— n denotes 1–5 m denotes 0,1

$R^1$, $R^2$ independently of one another denote hydrogen, lower alkyl or aryl or together they form a carbocyclic five-membered or six-membered ring, $R^3$ denotes hydrogen or a group —$OR^5$ or —$NR^6R^7$ $R^4$ denotes hydrogen or a group —$OR^5$ $R^5$ denotes hydrogen, lower alkyl, aryl or arylalkyl $R^6$ denotes hydrogen, lower alkyl or arylalkyl $R^7$ denotes hydrogen, lower alkyl, arylalkyl, acyl, alkylsulfonyl or arylsulfonyl $R^O$,$R^{OO}$ independently of one another denote hydrogen, lower alkyl, aryl, arylalkyl, hetaryl, acyl or an optionally substituted carbocyclic or heterocyclic ring or, together with the nitrogen to which they are bound, they form an optionally substituted five-membered or six-membered ring which can in addition contain 1 to 3 further heteroatoms or they denote a group

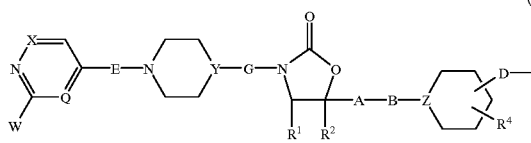

$R^{OOO}$ denotes hydrogen, lower alkyl, arylalkyl or a group $NHR^{OOO}$ $R^{OOOO}$ denotes hydrogen, lower alkyl, arylalkyl, acyl, alkylsulfonyl or arylsulfonyl as well as pharmacologically acceptable salts thereof.

Lower alkyl should in all cases represent a straight-chained or branched $C_1$–$C_6$ alkyl group such as methyl, ethyl, propyl, isopropyl, butyl, isobutyl, pentyl or hexyl in particular methyl, ethyl, propyl, isobutyl and pentyl.

Aryl usually denotes a phenyl residue which optionally is substituted once or several times.

Arylalkyl usually denotes an unsubstituted or a once or several-fold substituted benzyl, phenethyl, phenylpropyl, phenylbutyl or phenylpentyl residue preferably a benzyl, phenethyl or phenylpentyl residue. $C_1$–$C_6$ alkyl residues and preferably methyl, ethyl or isopropyl as well as chlorine, bromine, fluorine or hydroxy, methoxy, benzyloxy, acetyloxy, carboxy, ethoxy-carbonyl, aminocarbonyl, methylaminocarbonyl, dimethylaminocarbonyl, cyano, amino, methylamino, dimethylamino, benzylamino, acetylamino, benzoylamino and amidino group come into consideration as substituents.

Acyl usually denotes a formyl, acetyl, propionyl, butyryl or benzoyl residue, in particular an acetyl or benzoyl residue.

Alkylsulfonyl usually denotes a methanesulfonyl, ethanesulfonyl, propanesulfonyl or a butanesulfonyl residue, in particular a butanesulfonyl residue.

Arylsulfonyl usually denotes a benzene sulfonic acid or toluenesulfonic acid residue.

If the residues $R^1$ and $R^2$ together form a carbocyclic five-membered or six-membered ring, this is then a saturated or unsaturated 5-6-membered ring which is optionally substituted once or twice by lower alkyl such as a cyclopentyl, cyclohexyl, cyclopentenyl or cyclohexenyl ring.

Compounds of the general formula I contain at least one asymmetric carbon atom and therefore optically active compounds of the general formula I are also a subject matter of the present invention. In addition the present invention concerns conformational isomers of compounds of the general formula I which may occur.

Preferred compounds are compounds of formula I in which the group A-B represents a group $(CH_2)_{1-3}$ or $(CH_2)_{1-3}$—CO and Q, W, X, Y, Z, D, $R^1$, $R^2$ and $R^4$ have the stated meanings.

Compounds of formula I are particularly preferred in which the group A—B denotes a methylene, ethylene, carbonyl or methylenecarbonyl group and Q, W, X, Y and Z denote nitrogen.

Compounds of the general formula I are prepared according to well-known methods by hydrolyzing an ester of the general formula II

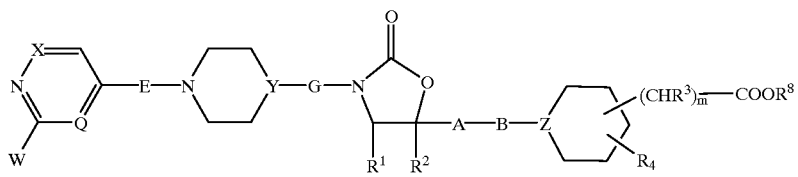

(II)

in which $R^1$, $R^2$, $R^3$, R, A, B, E, G, Q, W, X, Y, Z and m have the meanings given above and $R^8$ denotes methyl, ethyl, tert, butyl, phenyl or benzyl.

Compounds of the general formula II are prepared according to the reaction path shown in scheme 1.

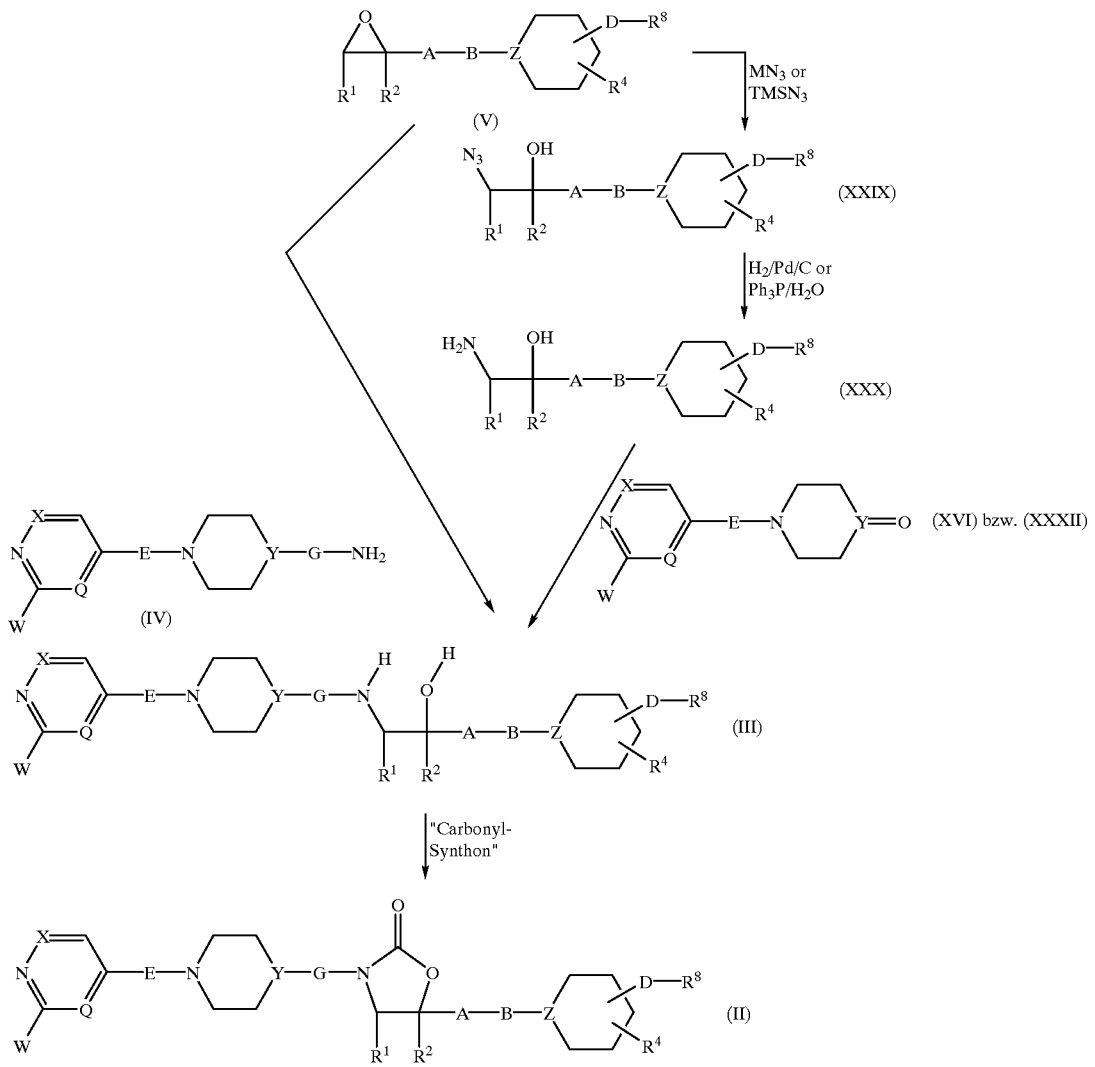

Scheme 1

$R^1$, $R^2$, $R^4$, $R^8$, A, B, D, E, G, Q, W, X, Y and Z have the aforementioned meanings in scheme 1. "Carbonyl synthon" usually denotes phosgene, diphosgene, triphosgene, carbonyldiimidazole, dimethyldiethyl carbonate or diphenyl carbonate, methyl chloroformate or ethyl chloroformate in particular carbonyldiimidazole, diethyl carbonate or ethyl chloroformate. $MN_3$ denotes a metal azide such as lithium, sodium, potassium, tributyltin or magnesium azide in particular lithium azide or sodium azide. $TMSN_3$ is the abbreviation for trimethylsilyl azide.

Compounds of the general formula IV can be prepared according to the reaction paths shown in scheme 2.

SCHEME 2
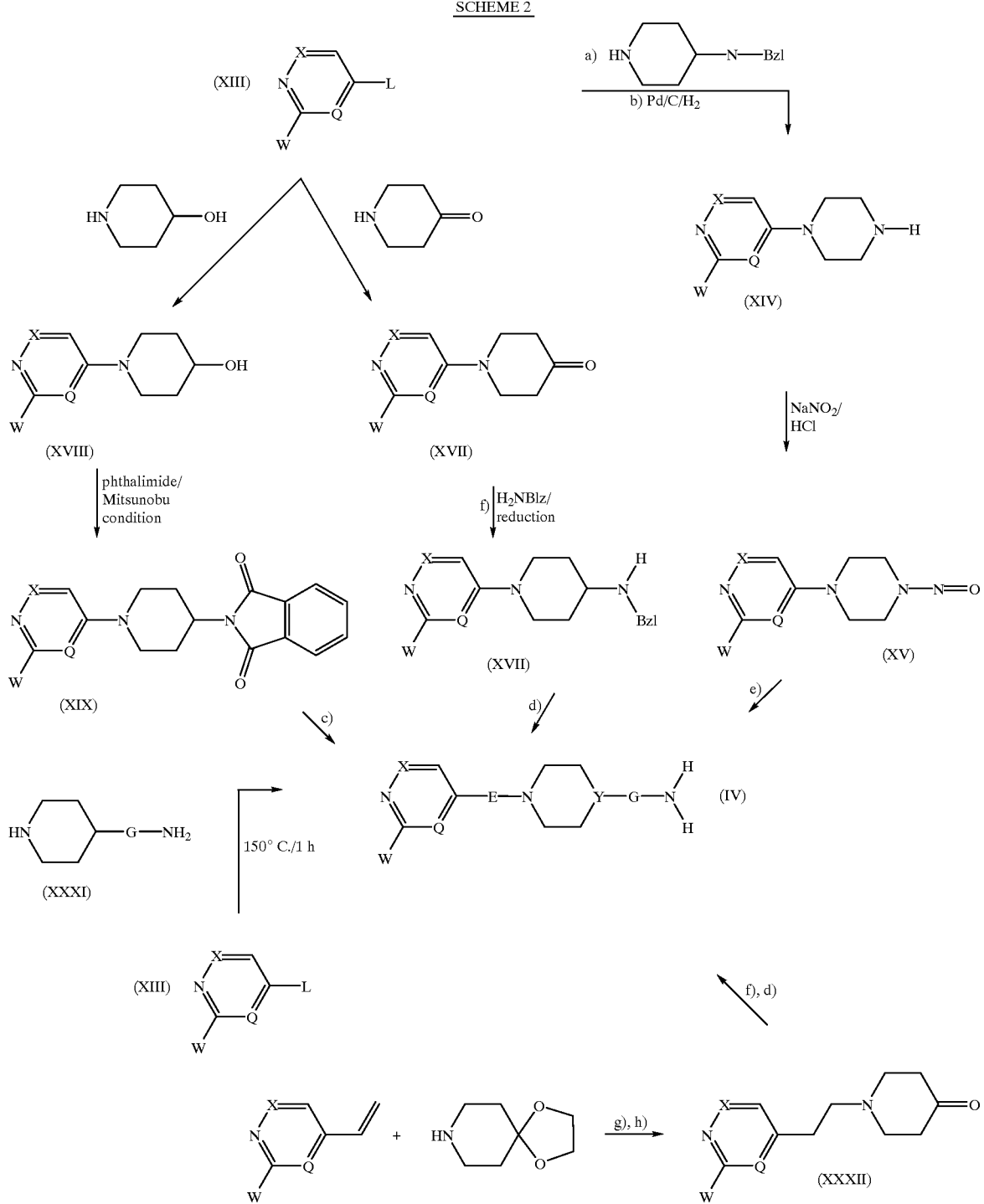
c) hydrolysis of the pththalimide; d) hydrogenation of benzyl the groups;
e) reduction of the nitroso group; g) AcOH/100° C./3 h; h) HCl/THF/H₂O
Scheme 2
E, G, Q, X and W have the aforementioned meanings in scheme 2; L usually denotes a leaving group such as chlorine, bromine, iodine, mesylate, triflate or tosylate in particular chlorine or tosylate.

Compounds of the general formula V can be prepared via reaction paths as shown in scheme 3.

SCHEME 3

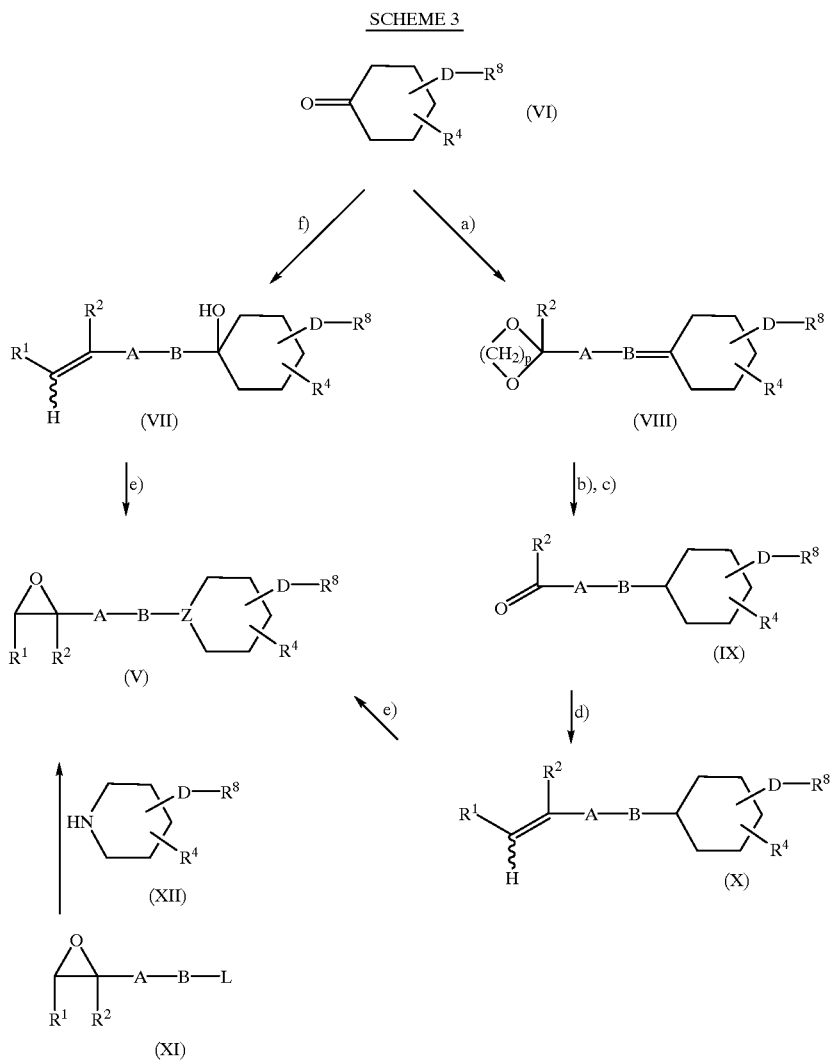

a) Wittig reaction; b) Pd/C/H$_2$; c) ketal cleavage; d) Wittig reaction; e) epoxidation; f) organometallic reaction Scheme 3

In scheme 3 R$^1$, R$^2$, R$^3$, R$^4$, A, B and L have the above-mentioned meanings and in the case that B denotes a carbonyl group L can also denote a hydroxyl group; p denotes the number 1 or 2.

Some of the compounds of the general formula VI are commercially available and can in special cases be obtained by oxidizing an alcohol of the general formula XX

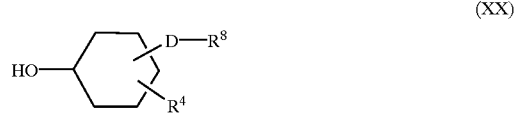

(XX)

in which D, R$^4$ and R$^8$ have the aforementioned meanings.

Compounds of the general formula Vii can be prepared by reacting a compound of the general formula VI with an organometallic compound of the general formula XXI (XXI)

in which R$^1$, R$^2$, A and B have the aforementioned meanings and M has the meaning of a metal such as lithium, magnesium or titanium.

Compounds of the general formula VIII are prepared according to known processes by reacting a compound of formula VI with a phosphorylide of the general formula XXII

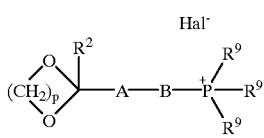

(XXII)

in which $R^2$, A, B and p have the aforementioned meanings, $R^9$ denotes butyl, phenyl or p-tolyl and Hal⁻ denotes chloride, bromide or iodide.

Compounds of the general formula XI are commercially available and can be prepared in special cases by epoxidizing an olefin of the general formula XXIII

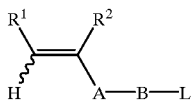

(XXIII)

in which $R^1$, $R^2$, A, B and L have the aforementioned meanings. Compounds of the general formula XXII are usually commercially available 2-piperidinecarboxylic acid derivatives; in special cases compounds of formula XII can be prepared by reacting a commercially available 3- or 4-piperidone of formula XXIV with a commercially available acetic acid ester of the general formula XXV

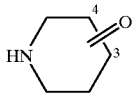

(XXIV)

in which $R^3$ and $R^8$ have the aforementioned meanings or with a Wittig reagent of the general formula XXVI

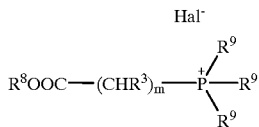

(XXVI)

in which $R^3$, $R^8$, $R^9$, m and Hal⁻ have the aforementioned meanings.

Some of the compounds of the general formula XX are commercially available and can in special cases be obtained according to known processes by hydrogenation of the nucleus of an aryl carboxylic acid of the general formula XXVII

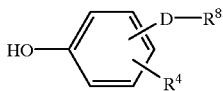

(XXVII)

in which $R^4$, $R^8$ and D have the aforementioned meanings.

Compounds of the general formula XXI are either commercially available or they can be synthesized in situ according to the general processes for the production of organometallic compounds.

Compounds of the general formula X can be obtained according to known processes by reacting a compound IX with a Wittig reagent of the general formula XXVIII

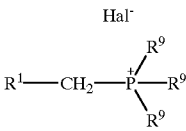

(XXVIII)

in which $R^1$, $R^9$ and Hal⁻ have the aforementioned meanings.

Some of the Wittig reagents of formula XXII or of formula XXVI or of formula XXVIII are commercially available and can be prepared from the corresponding commercially available halogen compounds and triphosphines.

Hydrolysis of an ester of the general formula II to form the corresponding carboxylic acid of the general formula I is carried out according to the usual methods by treating a carboxylic acid ester of the general formula II in water or in a mixture of water, tetrahydrofuran, dioxane, methanol or ethanol preferably in a water/tetrahydrofuran mixture with a hydroxide such as sodium, potassium or lithium hydroxide preferably sodium or lithium hydroxide or with an acid such as hydrochloric acid, sulfuric acid or trifluoroacetic acid preferably trifluoroacetic acid and at temperatures between room temperature and 80° C. preferably at room temperature.

Reaction of a compound of the general formula XIII with 1-benzylpiperazine or 4-hydroxy or 4-oxopiperidine (scheme 2) or the reaction of a compound of formula XI with a compound of formula XII or a compound of formula XI with an amine of formula XII is usually carried out in an aprotic solvent such as toluene, tetrahydrofuran, diethyl ether, dimethylformamide or methylene chloride, preferably dimethylformamide or tetrahydrofuran, using a base such as potassium hydride, sodium hydride, potassium carbonate or sodium bicarbonate, preferably sodium hydride or potassium carbonate, and at temperatures between room temperature and 180° C., preferably at 120° C. or room temperature.

The reaction between 3- or 4-piperidone of formula XXIV and an ester of formula XXV is carried out under the conditions of an aldol reaction in a solvent such as methanol, ethanol, toluene, tetrahydrofuran, diethyl ether or dimethylformamide, preferably tetrahydrofuran or dimethylformamide, using a base such as sodium or potassium methylate or ethylate, sodium hydride, potassium hydride, lithium diisopropylamide, potassium hexamethyldisilazide, preferably sodium hydride or lithium diisopropylamide, and at temperatures between −78° C. and 90° C., however, preferably between −78° C. and room temperature.

Benzyl protecting groups are removed if necessary by catalytic hydrogenation such as e.g. by palladium/carbon/hydrogen.

The Mitsunobu reaction between a compound of formula XVIII and phthalimide is carried out according to processes known from the literature (Mitsunobu O., Synthesis, page 1 (1981)).

A ketone of formula XVI is reductively aminated with dibenzylamine or an amine of formula XXX according to processes known from the literature by reacting the ketone and amine component in a solvent such as methanol or ethanol in the presence of a reducing agent such as sodium cyanoborohydride or sodium triacetateborohydride with addition of a Bronsted or Lewis acid such as hydrochloric acid, acetic acid, titanium tetrachloride or titanium tetraisopropylate and at a temperature between 0° C. and 100° C. preferably at room temperature or in the presence of a hydrogenation catalyst such as platinum dioxide and a hydrogen atmosphere (Borch R. F., Org. Synth. Coll. Vol. 6, 499 (1988); Heinzelman R. V. Z. Chem. 8, 270 (1968); Mattson R. F., J. Org. Chem. 55, 2552 (1990); Barney C. L. Tetr. Letters 31, 5547 (1990); Hutchins R. O., J. Org. Chem. 46, 3571 (1981)).

The nitrosation of a compound of the general formula XIV to form a compound of formula XV is usually carried out with sodium nitrite or isoamylnitrite in water or ethanol with addition of an acid such as hydrochloric acid or acetic acid and at a temperature between −20° C. and 80° C. preferably at room temperature.

The reduction of a nitroso compound of the general formula XV is carried out according to known processes by reacting a compound of formula XV in a solvent such as water, acetic acid, ethanol, tetrahydrofuran or diethyl ether, preferably acetic acid or tetrahydrofuran, with a reducing agent such as elemental zinc, lithium aluminium hydride or sodium aluminium hydride, preferably elemental zinc or lithium aluminium hydride, and at a temperature between room temperature and 120° C., however, preferably at 70° C. The conversion of a compound of the general formula XV into a compound of formula IV can also be carried out hydrogenolytically using a catalyst such as palladium/carbon (Hatt, H. H., Org. Synth. Coll. Vol. 2, 211 (1943); Schüler F. W., J. Amer. Chem. Soc. 73, 4996 (1951)). An alcohol of the general formula XX is oxidized to a ketone of the general formula VI according to known methods such as the Jones oxidation (Jones E. R. H., J. Chem. Soc. 36 (1946)), the Swern oxidation (Swern D., Tetrahedron 34, 1651 (1978)), the Dess-Martin oxidation (Dess D. B., Martin J. C., J. Org. Chem. 48, 4155 (1983)) or using a bromine-urotropine complex as an oxidizing agent (Yavari I., J. Chem. Res. (p) 274 (1994)).

If necessary the Wittig reagents used are prepared analogously to processes known from the literature (Buddras J., Angew. Chem. 80, 535 (1968): Bestmann H. J. Angew. Chem. 77, 620, 651 (1965); Wittig G. Ber. Deutsch. Chem. Ges. 88, 1654 (1955)).

The Wittig reaction is carried out according to known methods such as heating the reactants to reflux in an aprotic solvent such as benzene, toluene or xylene, preferably toluene.

The hydrolysis of phthalimide is usually carried out according to known methods by treating phthalimide with hydrazine hydrate or a semi-concentrated mineral acid such as hydrochloric acid or sulfuric acid, preferably with hydrazine hydrate or hydrochloric acid, at room temperature.

Amines are usually acylated in a solvent such as methylene chloride, dimethylformamide or pyridine, preferably methylene chloride or pyridine, with addition of an auxiliary base such as triethylamine or 4-dimethylaminopyridine and at a temperature between −10° C. and 50° C., however, preferably at room temperature.

A ketal of the general formula VIII is cleaved according to standard methods of organic chemistry ("ORGANIKUM; VEB Deutscher Verlag der Wissenschaften, Berlin 1977, page 486, 490).

Olefinic double bonds are catalytically hydrogenated analogously to processes known from the literature (A. Nose, Chem. Pharm. Bull. 38, 2097 (1990); Tamura M. Bull. Chem. Soc. Jpn. 53, 561 (1980); Liu H.-J., Synth. Commun. 15, 965 (1985); Chido N., J. Chem. Soc. Chem. Commun. 994 (1990); Buchi G., J. Amer. Chem. Soc. 89, 6745 (1967); Ernst I., Coll. Czech. Chem. Comm. 24, 3341 (1959); Johnson W. S., J. Amer. Chem. Soc. 79, 1995 (1957); Muchowski J. M., Can J. Chem. 47, 857 (1969)).

An olefin of formula VII or of formula X or of formula XXIII is epoxidized according to processes known from the literature by reaction with a peroxy acid such as m-chloroperbenzoic acid, peracetic acid or trifluoroperacetic acid, preferably m-chloroperbenzoic acid, in an aprotic solvent such as methylene chloride and at a temperature between −30° C. and 50° C., preferably room temperature; in addition the olefins mentioned above can be converted into the corresponding epoxides by means of the Sharpless epoxidation (Sharpless K. B., Org. Syntheses, Vol. 63, 66 (1985)).

The organometallic reaction mentioned in scheme 3 is usually a Grignard reaction which is carried out by processes known from the literature. However, if necessary the magnesium reagent of formula XXI can be transferred into a lithium or titanium reagent before reacting it with a carbonyl compound of formula VI (Reetz M. T., Chem. Ber. 118, 1421 (1985)).

An aminoalcohol of formula III is converted into an oxazolidinone of formula II according to processes known from the literature by reacting an aminoalcohol of formula III with diethyl carbonate (Evans D. A., Org. Syntheses, vol. 68, 77 (1989)) or carbonyldiimidazole (Chadwick D. I., J. Chem. Soc. Perkin Trans. 481 (1984); Geffken D. Arch. Pharm. 313, 817 (1980)) or phosgene (Newman W. S., J. Am. Chem. Soc. 73, 4199 (1951)) or diphosgene or triphosgene (Hassner A., Synth. Commun. 23, 2839 (1993)), or a methyl, ethyl or benzyl ester of chloroformic acid (Kanoshinzo, J. Org. Chem. 53, 3865 (1988)) in a solvent such as methylene chloride, dimethylformamide, toluene, dioxane, tetrahydrofuran, water or diethyl ether, preferably dimethylformamide, methylene chloride or tetrahydrofuran, and at a temperature between −50° C. and 80° C. preferably at room temperature.

Catalytic hydrogenation of a compound of formula XXVII is carried out in a solvent such as methanol or ethanol with addition of a catalyst such as ruthenium oxide, rhodium oxide or palladium/strontium carbonate, preferably rhodium oxide, in a hydrogen atmosphere at a pressure of 1–200 bar, preferably at 200 bar, and at a temperature between room temperature and 200° C. (Rastin R. H., I. Chem. Soc. 1855 (1949).

The opening of an epoxide of formula V with an amine of formula IV usually takes place in a solvent such as methanol, ethanol, dimethylformamide or toluene, preferably ethanol or toluene, and at a temperature between 0° C. and 120° C., preferably 80° C.

The opening of an epoxide of formula V with a metal azide is carried out according to methods known from the literature by reacting an epoxide of formula V with a metal azide such as lithium, sodium, potassium, tributyltin or magnesium azide, preferably sodium azide, in a solvent such as methanol, ethanol, 1,4-dioxane, water, dimethylformamide, tetrahydrofuran, acetonitrile or hexamethylphosphorotriamide or in mixtures of the said solvents, but preferably in methanol, dimethyl-formamide or 1,4-dioxane-water mixtures, and at a reaction temperature between −10° C. and 120° C., preferably 80° C. (Vanderverf C. A., J. Am. Chem. Soc. 76, 1231 (1954); Saito S. Tetrahedron Lett. 30, 4153 (1989); Hudlicky T., J. Chem. Soc. Perkin Trans. I, 2907 (1991)). An epoxide of formula V is usually reacted with trimethylsilylazide in a solvent such as methanol, tetrahydrofuran, methylene chloride, chloroform, dichloroethane or benzene, preferably tetrahydrofuran or methylene chloride, without further additives or using additives such as titanium tetraisopropylate, aluminium triisopropylate, dichlorotitanium diisopropylate or diethylaluminium fluoride, preferably titanium tetraisopropylate or aluminium triisopropylate and at a temperature between 0° C. and 100° C., but preferably at room temperature (Emziane M., Synthesis, p. 541 (1988); Saito S., Tetrahedron Lett. 26, 5309 (1985); Blandy C., Tetrahedron Lett. 24, 4189 (1983); Jung M. E., J. Org. Chem. 56, 2614 (1991)).

An azide of formula XXIX is converted into an amine of formula XXX according to known methods: Suami T., Bull. Chem. Soc. Jpn., 51, 855 (1978); Boullanger P., Bull. Soc. Chim. Fr., p. 2149 (1973); Ackerman K., Can. J. Chem., 50, 3886 (1972); Hanessian S., Chem. Ind., p. 1296 (1965); Horner L., Liebigs Ann. Chem., 591, 117 (1955); Koziara A. Synthesis, p. 487 (1987); Vogel E., Ang. Chem. Int. Ed. Engl., 18, 962 (1979); Purwono B., Synlett, 3, 231 (1992).

Compounds of formula I contain one or several chiral centres and can thus be present in a racemic or optically active form. Racemates can be separated mechanically or chemically into their enantiomers by well-known methods. Diastereomers are preferably formed from the racemic mixture by reaction with an optically active acid such as the D and L forms of tartaric acid, diacetyltartaric acid, dibenzoyl tartaric acid, mandelic acid, malic acid, lactic acid or the various optically active camphor sulfonic acids such as β-camphor sulfonic acid.

It is of course also possible to obtain optically active compounds of formula I by the above-mentioned methods by using starting materials (e.g. those of formula II) which are already optically active.

Alkaline salts, ammonium salts, trifluoroacetates or hydrochlorides are used above all as pharmacologically acceptable salts which are usually produced for example by titrating the compounds with inorganic or organic bases or acids such as sodium or potassium bicarbonate, sodium hydroxide solution, potassium hydroxide solution, aqueous ammonia or amines such as trimethylamine or triethylamine, trifluoroacetic acid or hydrochloric acid. The salts are usually purified by precipitation from water/acetone.

The new substances of formula I and salts thereof according to the invention can be administered enterally or parenterally in a liquid or solid form. In this connection all the usual forms of administration come into consideration such as tablets, capsules, coated tablets, syrups, solutions, suspensions etc. Water is preferably used as the injection medium which contains the usual additives in injection solutions such as stabilizing agents, solubilizers and buffers.

Such additives are for example tartrate and citrate buffer, ethanol, complexing agents (such as ethylenediaminetetraacetic acid and non-toxic salts thereof), high molecular polymers (such as liquid polyethylene oxide) in order to regulate viscosity. Liquid carriers for injection solutions have to be sterile and are preferably dispensed into ampoules. Solid carriers are e.g. starch, lactose, mannitol, methylcellulose, talcum, highly dispersed silicic acids, higher molecular fatty acids (such as stearic acid), gelatin, agar-agar, calcium phosphate, magnesium stearate, animal and vegetable fats, solid high molecular polymers (such as polyethylene glycols); preparations that are suitable for oral application can optionally contain flavourings and sweeteners.

The dose can depend of various factors such as the manner of administration, species, age or/and individual state of health. The doses to be administered daily are about 10–1000 mg/human, preferably 100–500 mg/human and can be taken once or distributed over several doses.

Within the sense of the present invention the following pyridine and pyridazine derivatives are preferred in addition to the compounds mentioned in the examples and compounds derived by combination of all meanings of substituents mentioned in the claims:

1) 1-{2-[2-Oxo-3-(3,4,5,6-tetrahydro-2H-[1,4']bipyridinyl-4-yl)-oxazolidin-5-yl]-ethyl}-piperidine-4-carboxylic acid
2) 1-{3-[2-Oxo-3-(3,4,5,6-tetrahydro-2H-[1,4']bipyridinyl-4-yl)-oxazolidin-5-yl]-propyl}-piperidine-4-carboxylic acid
3) 1-{4-[2-Oxo-3-(3,4,5,6-tetrahydro-2H-[1,4']bipyridinyl-4-yl)-oxazolidin-5-yl]-butyl}-piperidine-4-carboxylic acid
4) 1-{5-[2-Oxo-3-(3,4,5,6-tetrahydro-2H-[1,4']bipyridinyl-4-yl)-oxazolidin-5-yl]-pentyl}-piperidine-4-carboxylic acid
5) 1-[2-Oxo-5-phenyl-3-(3,4,5,6-tetrahydro-2H-[1,4']bipyridinyl-4-yl)-oxazolidin-5-ylmethyl]-piperidine-4-carboxylic acid
6) 1-[2-oxo-3-(3,4,5,6-tetrahydro-2H-[1,4']bipyridinyl-4-yl)-oxazolidine-5-carbonyl]-piperidine-4-carboxylic acid
7) 1-{2-[2-Oxo-3-(3,4,5,6-tetrahydro-2H-[1,4']bipyridinyl-4-yl)-oxazolidin-5-yl]-acetyl}-piperidine-4-carboxylic acid
8) 1-{5-[2-Oxo-3-(3,4,5,6-tetrahydro-2H-[1,4']bipyridinyl-4-yl)-oxazolidin-5-yl]-pentanoyl}-piperidine-4-carboxylic acid
9) 1-(2-Oxo-3-(4-pyridin-4-yl-piperazin-1-yl)-oxazolidin-5-ylmethyl]-piperidine-4-carboxylic acid
10) {1-[2-Oxo-3-(3,4,5,6-tetrahydro-2H-[1,4']bipyridinyl-4-yl)-oxazolidin-5-ylmethyl]-piperidin-3-yl}-acetic acid
11) (1-{2-[2-Oxo-3-(3,4,5,6-tetrahydro-2H-[1,4']bipyridinyl-4-yl)-oxazolidin-5-yl]-ethyl}-piperidin-3-yl}-acetic acid
12) {1-[2-Oxo-3-(3,4,5,6-tetrahydro-2H-[1,4']bipyridinyl-4-yl)-oxazolidin-5-carbonyl]-piperidin-3-yl}-acetic acid
13) (1-{4-[2-Oxo-3-(3,4,5,6-tetrahydro-2H-[1,4']bipyridinyl-4-yl)-oxazolidin-5-yl]-butyryl}-piperidin-3-yl)-acetic acid
14) (3-Hydroxy-1-{5-[2-oxo-3-(3,4,5,6-tetrahydro-2H-[1,4']bipyridinyl-4-yl)-oxazolidin-5-yl]-pentanoyl}-piperidin-3-yl)-acetic acid
15) (3-Hydroxy-1-{2-[2-oxo-3-(3,4,5,6-tetrahydro-2H-[1,4']bipyridinyl-4-yl)-oxazolidin-5-yl]-acetyl}-piperidin-3-yl)-acetic acid
16) {3-Hydroxy-1-[2-oxo-3-(3,4,5,6-tetrahydro-2H-[1,4']-bipyridinyl-4-yl)-oxazolidine-5-carbonyl]-piperidin-3-yl}-acetic acid
17) {3-Hydroxy-1-[2-oxo-3-(3,4,5,6-tetrahydro-2H-[1,4']bipyridinyl-4-yl)-oxazolidin-5-ylmethyl]-piperidin-3-yl}-acetic acid
18) (3-Hydroxy-1-{4-[2-oxo-3-(3,4,5,6-tetrahydro-2H-[1,4']bipyridinyl-4-yl)-oxazolidin-5-yl]-butyl}-piperidin-3-yl)-acetic acid
19) {1-[2-Oxo--4-phenyl-3-(3,4,5,6-tetrahydro-2H-[1,4']bipyridinyl-4-yl)-oxazolidin-5-ylmethyl]-piperidin-4-yl}-acetic acid
20) {4-Hydroxy-1-[2-oxo-5-phenyl-3-(3,4,5,6-tetrahydro-2H-[1,4']bipyridinyl-4-yl)-oxazolidine-5-carbonyl]-piperidin-4-yl}-acetic acid
21) {1-[4-Methyl-2-oxo-3-(3,4,5,6-tetrahydro-2H-[1,4']bipyridinyl-4-yl)-oxazolidine-5-carbonyl]-piperidin-4-yl}-acetic acid
22) {1-[4-Methyl-2-oxo-3-(3,4,5,6-tetrahydro-2H-[1,4']bipyridinyl-4-yl)-oxazolidine-5-carbonyl]-piperidin-3-yl}-acetic acid 23) {3-Hydroxy-1-[5-methyl-2-oxo-3-(3,4,5,6-tetrahydro-2H-[1,4']bipyridinyl-4-yl)-oxazolidine-5-carbonyl]-piperidin-3-yl}-acetic acid
24) 1-[2-Oxo-5-phenyl-3-(3,4,5,6-tetrahydro-2H-[1,4']bipyridinyl-4-yl)-oxazolidine-5-carbonyl]-piperidine-4-carboxylic acid
25) (1-{2-[2-Oxo-3-(3,4,5,6-tetrahydro-2H-[1,4']bipyridinyl-4-yl)-oxazolidin-5-yl]-ethyl}-piperidin-4-yl)-acetic acid
26) (1-{4-[2-Oxo-3-(3,4,5,6-tetrahydro-2H-[1,4']bipyridinyl-4-yl)-oxazolidin-5-yl]-butyl}-piperidin-4-yl)-acetic acid
27) (4-Hydroxy-1-{2-[2-oxo-3-(3,4,5,6-tetrahydro-2H-[1,4']bipyridinyl-4-yl)-oxazolidin-5-yl]-ethyl}-piperidin-4-yl)-acetic acid
28) (4-Hydroxy-1-{5-[2-oxo-3-(3,4,5,6-tetrahydro-2H-[1,4']bipyridinyl-4-yl)-oxazolidin-5-yl]-pentyl}-piperidin-4-yl)-acetic acid
29) (1-{2-[2-Oxo-3-(3,4,5,6-tetrahydro-2H-[1,4']bipyridinyl-4-yl)-oxazolidin-5-yl]-acetyl}-piperidin-4-yl)-acetic acid
30) (1-{5-[2-Oxo-3-(3,4,5,6-tetrahydro-2H-[1,4']bipyridinyl-4-yl)-oxazolidin-5-yl]-pentanoyl}-piperidin-4-yl)-acetic acid
31) (4-Hydroxy-1-{2-[2-oxo-3-(3,4,5,6-tetrahydro-2H-[1,4']bipyridinyl-4-yl)-oxazolidin-5-yl]-acetyl}-piperidin-4-yl)-acetic acid
32) (4-Hydroxy-1-{4[2-oxo-3-(3,4,5,6-tetrahydro-2H-[1,4']bipyridinyl-4-yl)-oxazolidin-5-yl]-butyryl}-piperidin-4-yl)-acetic acid
33) {1-[2-Oxo-3-(3,4,5,6-tetrahydro-2H-[1,4']bipyridinyl-4-yl)-oxazolidine-5-carbonyl]-piperidin-4-yl)-acetic acid
34) {4-Hydroxy-1-[2-oxo-3-(3,4,5,6-tetrahydro-2H-[1,4']bipyridinyl-4-yl)-oxazolidine-5-carbonyl]-piperidin-4-yl)-acetic acid
35) 1-{2-[2-Oxo-3-(3,4,5,6-tetrahydro-2H-[1,4']bipyridinyl-4-yl)-oxazolidin-5-yl]-ethyl}-piperidine-3-carboxylic acid
36) 1-{4-[2-Oxo-3-(3,4,5,6-tetrahydro-2H-[1,4']bipyridinyl-4-yl)-oxazolidin-5-yl]-butyl}-piperidine-3-carboxylic acid
37) 1-[2-Oxo-3-(3,4,5,6-tetrahydro-2H-[1,4']bipyridinyl-4-yl)-oxazolidine-5-carbonyl]-piperidine-3-carboxylic acid
38) 1-{4-[2-Oxo-3-(3,4,5,6-tetrahydro-2H-[1,4']bipyridinyl-4-yl)-oxazolidin-5-yl]-butyryl}-piperidine-3-carboxylic acid
39) 1-[2-Oxo-3-(3,4,5,6-tetrahydro-2H-[1,4']bipyridinyl-4-yl)-oxazolidin-5-ylmethyl]-piperidine-2-carboxylic acid
40) 1-{5-[2-Oxo-3-(3,4,5,6-tetrahydro-2H-[1,4']bipyridinyl-4-yl)-oxazolidin-5-yl]-pentyl}-piperidine-2-carboxylic acid
41) 1-{4-[2-Oxo-3-(3,4,5,6-tetrahydro-2H-[1,4']bipyridinyl-4-yl)-oxazolidin-5-yl]-butyryl}-piperidine-2-carboxylic acid
42) 1-[2-Oxo-3-(3,4,5,6-tetrahydro-2H-[1,4']bipyridinyl-4-yl)-oxazolidine-5-carbonyl]-piperidine-2-carboxylic acid
43) 1-{2-[5-Methyl-2-oxo-3-(3,4,5,6-tetrahydro-2H-[1,4']bipyridinyl-4-yl)-oxazolidin-5-yl]-ethyl}-piperidine-2-carboxylic acid
44) 1-{5-[4-Methyl-2-oxo-3-(3,4,5,6-tetrahydro-2H-[1,4']bipyridinyl-4-yl)-oxazolidin-5-yl]-pentyl}-piperidine-2-carboxylic acid
45) 1-{4-[5-Methyl-2-oxo-3-(3,4,5,6-tetrahydro-2H-[1,4']bipyridinyl-4-yl)-oxazolidin-5-yl]-butyryl}-piperidine-2-carboxylic acid
46) 1-{5-[4-Methyl-2-oxo-3-(3,4,5,6-tetrahydro-2H-[1,4']bipyridinyl-4-yl)-oxazolidin-5-yl]-pentanoyl}-piperidine-2-carboxylic acid
47) 1-[2-Oxo-3-(4-pyridazin-4-yl-piperazin-1-yl)-oxazolidin-5-ylmethyl]-piperidine-4-carboxylic acid
48) 1-[2-Oxo-3-(1-pyridazin-4-yl-piperidin-4-yl)-oxazolidin-5-ylmethyl]-piperidine-4-carboxylic acid
49) 1-[2-Oxo-3-(1-pyridazin-4-yl-piperidin-4-yl)-oxazolidine-5-carbonyl]-piperidine-4-carboxylic acid
50) 1-[2-Oxo-3-(4-pyridinyl-4-yl-piperazin-1-yl)-oxazolidine-5-carbonyl]-piperidine-4-carboxylic acid
51) 1-[2-Oxo-3-(4-pyridazin-4-yl-piperazin-1-yl)-oxazolidine-5-carbonyl]-piperidin-4-carboxylic acid
52) {1-[2-Oxo-3-(1-pyridazin-4-yl-piperidin-4-yl)-oxazolidin-5-ylmethyl]-piperidin-4-yl}-acetic acid
53) {4-Hydroxy-1-[2-oxo-3-(4-pyridazin-4-yl-piperazin-1-yl)-oxazolidin-5-yl]-piperidin-4-yl}-acetic acid
54) 1-{3-[2-Oxo-3-(4-pyridazin-4-yl-piperazin-1-yl)-oxazolidin-5-yl]-propyl}-piperidine-4-carboxylic acid
55) 1-{3-[4-Methyl-2-oxo-3-(4-pyridazin-4-yl-piperazin-1-yl)-oxazolidin-5-yl]-propionyl}-piperidine-4-carboxylic acid
56) 1-[4-Methyl-2-oxo-3-(4-pyridin-4-yl-piperazin-1-yl)-oxazolidin-5-ylmethyl]-piperidine-4-carboxylic acid
57) (Butane-1-sulfonylamino)-{1-[4-methyl-2-oxo-3-(3,4,5,6-tetrahydro-2H-[1,4']bipyridinyl-4-yl)-oxazolidin-5-ylmethyl]-piperidin-4-yl}-acetic acid
58) (Butane-1-sulfonylamino)-(1-{3-[2-oxo-3-(3,4,5,6-tetrahydro-2H-[1,4']bipyridinyl-4-yl)-oxazolidin-5-yl]-propyl}-piperidin-4-yl)-acetic acid
59) (Butane-1-sulfonylamino)-(1-[2-oxo-3-(3,4,5,6-tetrahydro-2H-[1,4'] bipyridinyl-4-yl)-oxazolidine-5-carbonyl]-piperidin-4-yl)-acetic acid
60) 4-[2-Oxo-3-(3,4,5,6-tetrahydro-2H-[1,4']bipyridinyl-4-yl)-oxazolidin-5-yl]-cyclohexanecarboxylic acid
61) 4-[2-Oxo-3-(3,4,5,6-tetrahydro-2H-[1,4']bipyridinyl-4-yl)-oxazolidin-5-ylmethyl]-cyclohexanecarboxylic acid
62) 4-{3-[2-Oxo-3-(3,4,5,6-tetrahydro-2H-[1,4']bipyridinyl-4-yl)-oxazolidin-5-yl]-propyl}-cyclohexanecarboxylic acid
63) 3-[2-Oxo-3-(3,4,5,6-tetrahydro-2H-[1,4']bipyridinyl-4-yl)-oxazolidin-5-yl]cyclohexanecarboxylic acid
64) 4-Hydroxy-4-{3-[2-oxo-3-(3,4,5,6-tetrahydro-2H-[1,4']bipyridinyl-4-yl)-oxazolidin-5-yl]-propyl}-cyclohexanecarboxylic acid
65) {4-[2-Oxo-3-(3,4,5,6-tetrahydro-2H-[1,4']bipyridinyl-4-yl)-oxazolidin-5-yl]-cyclohexyl}-acetic acid
66) [4-Hydroxy-4-{3-[2-oxo-3-(3,4,5,6-tetrahydro-2H-[1,4']bipyridinyl-4-yl)-oxazolidin-5-yl]-propyl}-cyclohexyl}-acetic acid
67) {1,4-Dihydroxy-4-[2-oxo-3-(3,4,5,6-tetrahydro-2H-[1,4']bipyridinyl-4-yl)-oxazolidin-5-ylmethyl]-cyclohexyl}-acetic acid
68) 3-{2-[2-Oxo-3-(3,4,5,6-tetrahydro-2H-[1,4']bipyridinyl-4-yl)-oxazolidin-5-yl]-ethyl}-cyclohexanecarboxylic acid
69) 2-{4-[2-Oxo-3-(3,4,5,6-tetrahydro-2H-[1,4']bipyridinyl-4-yl)-oxazolidin-5-yl]-butyl}-cyclohexanecarboxylic acid
70) 4-[4-Methyl-2-oxo-3-(3,4,5,6-tetrahydro-2H-[1,4']bipyridinyl-4-yl)-oxazolidin-5-ylmethyl]-cyclohexanecarboxylic acid
71) 4-[2-Oxo-3-(1-pyridazin-4-yl-piperidin-4-yl)-oxazolidin-5-ylmethyl]-cyclohexanecarboxylic acid
72) 4-[2-Oxo-3-(4-pyridazin-4-yl-piperazin-1-yl)-oxazolidin-5-ylmethyl]-cyclohexanecarboxylic acid
73) (Butane-1-sulfonylamino)-{4-[4,5-dimethyl-2-oxo-3-(4-(pyridazin-4-yl-piperazin-1-yl)-oxazolidin-5-ylmethyl]-1-hydroxy-cyclohexyl}-acetic acid
74) 1-[2-Oxo-3-(3,4,5,6-tetrahydro-2H-[1,4']bipyridinyl-4-yl-4-(3,4,5-trimethoxyphenyl)-oxazolidine-5-carbonyl]-piperidine-4-carboxylic acid. f.p. 108–114° C.

75) 1-[4-(3,4-Dimethoxy-phenyl)-2-oxo-3-(3,4,5,6-tetrahydro-2H-[1,4']bipyridinyl-4-yl)-oxazolidine-5-carbonyl]-piperidine-4-carboxylic acid. f.p. 118° C.
76) 1-[4-(4-Cyano-phenyl)-2-oxo-3-(3,4,5,6-tetrahydro-2H-[1,4']bipyridinyl-4-yl)-oxazolidine-5-carbonyl]-piperidine-4-carboxylic acid. f.p. 100–105° C.
77) 1-[4-Methyl-2-oxo-3-(3,4,5,6-tetrahydro-2H-[1,4']bipyridinyl-4-yl)-oxazolidine-5-carbonyl]-piperidine-4-carboxylic acid. f.p. 73–75° C.
78) (5S)-1-[5-Methyl-2-oxo-3-(3,4,5,6-tetrahydro-2H-[1,4']bipyridinyl-4-yl)-oxazolidin-5-ylmethyl]-piperidine-4-carboxylic acid. f.p. 223° C. (decomp.)
79) 1-[2-Oxo-3-(3,4,5,6-tetrahydro-2H-[1,4']bipyridinyl-4-yl)-4-(3-trifluoromethylphenyl)-oxazolidin-5-ylmethyl]-piperidine-4-carboxylic acid. f.p. 125–130° C.
80) 1-[4-(4-Chlorophenyl)-2-oxo-3-(3,4,5,6-tetrahydro-2H-[1,4']bipyridinyl-4-yl)-oxazolidin-5-ylmethyl]-piperidine-4-carboxylic acid. f.p. 110–115° C.
81) 1-[4-(4-Isopropylphenyl)-2-oxo-3-(3,4,5,6-tetrahydro-2H-[1,4']bipyridinyl-4-yl)-oxazolidin-5-ylmethyl]-piperidine-4-carboxylic acid
82) 1-[4-(4-tert.-Butyl-phenyl)-2-oxo-3-(3,4,5,6-tetrahydro-2H-[1,4']bipyridinyl-4-yl)-oxazolidin-5-ylmethyl]-piperidine-4-carboxylic acid
83) 1-{3-[1-(2-Amino-pyrimidin-4-yl)-piperidin-4-yl]-2-oxo-oxazolidin-5ylmethyl}-piperidine-4-carboxylic acid
84) 1-{2-Oxo-3-[1-(2-piperidin-1-yl-pyrimidin-4-yl)-piperidin-4-yl]-oxazolidin-5-ylmethyl}-piperidine-4-carboxylic acid
85) 1-{2-Oxo-3-[1-(2-phenylamino-pyrimidin-4-yl)-piperidin-4-yl]-oxazolidin-5-ylmethyl}-piperidine-4-carboxylic acid
86) 1-{2-Oxo-3-{1-[2-(pyrimidin-2-ylamino)-pyrimidin-4-yl]-piperidin-4-yl}-oxazolidin-5-ylmethyl)-piperidine-4-carboxylic acid
87) 1-{3-[1-(2-Amino-pyrimidin-4-yl)-piperidin-4-yl]-2-oxo-hexahydro-benzooxazol-7a-ylmethyl}-piperidine-4-carboxylic acid
88) 1-{3-[1-(2-Benzylamino-pyrimidin-4-yl)-piperidin-4-yl]-2-oxo-hexahydrocyclopentaoxazol-6a-ylmethyl}-piperidine-4-carboxylic acid
89) 1-{3-[1-(2-Guanidino-pyrimidin-4-yl)-piperidin-4-yl]-2-oxo-oxazolidin-5-ylmethyl}-piperidine-4-carboxylic acid
90) 1-{3-[1-(2-Acetimidoylamino-pyrimidin-4-yl)-piperidin-4-yl]-2-oxo-oxazolidin-5-ylmethyl}-piperidine-4-carboxylic acid
91) 1-{3-[1-(2-Amino-pyrimidin-4-yl)-piperidin-4-yl]-4-ethyl-2-oxo-oxazolidin-5-ylmethyl}-piperidine-4-carboxylic acid
92) 1-[4-Ethyl-2-oxo-3-(3,4,5,6-tetrahydro-2H-[1,4']bipyridinyl-4-yl)-oxazolidin-5-ylmethyl]-piperidine-4-carboxylic acid
93) 1-[4-Butyl-2-oxo-3-(3,4,5,6-tetrahydro-2H-[1,4']bipyridinyl-4-yl)-oxazolidin-5-ylmethyl]-piperidine-4-carboxylic acid
94) 1-[2-Oxo-4-pentyl-3-(3,4,5,6-tetrahydro-2H-[1,4']bipyridinyl-4-yl)-oxazolidin-5-ylmethyl]-piperidine-4-carboxylic acid
95) 1-[4-Hexyl-2-oxo-2-(3,4,5,6-tetrahydro-2H-[1,4']bipyridinyl-4-yl)-oxazolidin-5-ylmethyl]-piperidine-4-carboxylic acid
96) 1-[2-Oxo-3-(3,4,5,6-tetrahydro-2H-[1,4']bipyridinyl-4-yl)-4-(2-p-tolyl-ethyl)-oxazolidin-5-ylmethyl]-piperidine-4-carboxylic acid
97) 1-{3-[1-(2-Benzylamino-pyrimidin-4-yl)-piperidin-4-yl]-4-butyl-2-oxo-oxazolidin-5-ylmethyl}-piperidine-4-carboxylic acid The following examples show some process variants which can be used to synthesize the compounds according to the invention. However, they are not intended to limit the subject matter of the invention. The structure of the compounds was ascertained by means of $^1$H and optionally by $^{13}$C-NMR spectroscopy as well as by mass spectrometry. The purity of the substances was determined by means of C, H, N and by thin layer chromatography.

EXAMPLE 1

1-[(5S)-2-oxo-3-(3,4,5,6-tetrahydro-2H-[1,4']bipyridinyl-4-yl)-oxazolidin-5-ylmethyl]-piperidine-4-carboxylic acid a) A solution of 46 g (0.4 mol) 4-chloropyridine and 123.5 g (0.86 mol) 4-piperidone ethylene ketal is heated for 48 hours to reflux in 400 ml p-xylene. Subsequently the reaction mixture is cooled, the precipitated precipitate is removed by filtration, the mother liquor is concentrated to dryness and the residue is purified by column chromatography on silica gel (ethyl acetate/saturated ammonia-alkaline methanol 9/1). In this way 79.7 g (90%) 8-pyridin-4-yl-1,4-dioxa-8-aza-spiro[4.5]decane is obtained as a white powder. m/e=220; f.p.=65° C.

b) A solution of 79.7 g of the ketal prepared in a) in 2 l tetrahydrofuran is admixed with 1 1 6 n hydrochloric acid and the reaction mixture is stirred for 2 h at room temperature. Subsequently the tetrahydrofuran is removed in a vacuum on a rotary evaporator, the hydrochloric acid is made alkaline with semi-concentrated ammonium hydroxide solution and extracted four times with 100 ml methylene chloride each time. After drying the combined organic extracts over sodium sulfate and removing the solvent, the residue is purified by means of column chromatography on silica gel. 64.2 g (100% yield) 2,3,5,6-tetrahydro-[1,4']bipyridinyl-4-one is obtained in this manner as a grey powder. m/e=176; f.p.=102° C.

c) A solution of 32 g of the ketone produced in b) and 19.9 ml benzylamine in 400 ml methylene chloride is admixed in portions with 50.4 g sodium triacetate-borohydride while cooling on ice. Subsequently 12 ml 100% acetic acid is added dropwise, the reaction mixture is then allowed to stir for 4 h at room temperature and is afterwards admixed with 100 ml water. After separating the phases, the aqueous phase is made alkaline to pH 12 with 2 n sodium hydroxide solution and extracted five times with 50 ml methylene chloride each time. After drying the combined organic extracts over sodium sulfate and removing the solvent on a rotary evaporator, the benzyl-(3,4,5,6-tetrahydro-2H-[1,4']-bipyridinyl-4-yl)-amine obtained in this manner is taken up in 100 ml methanol and the solution is admixed with 3.5 g 10% palladium/carbon. The methanolic mixture is then hydrogenated at room temperature until the uptake of hydrogen is completed (30 h), the catalyst is then removed by filtration and the mixture is concentrated on a rotary evaporator. 22 g 3,4,5,6-tetrahydro-2H-[1,4']bipyridinyl-4-ylamine is obtained in this way as a light-yellow viscous oil which slowly crystallizes. m/e=177; $^1$H-NMR (d$^6$-DMSO); δ=8.10 ppm (d, 2H); 6.85 ppm (d, 2H); 3.80 ppm (d with fine resolution, 2H); 2.85 ppm (t with fine resolution, 2H); 2.70 ppm (m, 1H); 1.70 ppm (d with fine resolution, 2H); 1.20 ppm (q with fine resolution, 2H); f.p.=68° C.

d) A mixture of 5.7 g (2R)-glycidyl-tosylate (Fluka GmbH), 4 ml piperidine-4-carboxylic acid ethyl ester and 3.5 g potassium carbonate in 100 ml acetonitrile is heated for 2 h under reflux. After cooling the reaction mixture is admixed with 50 ml water and extracted three times each with 50 ml methylene chloride and 50 ml diethyl ether. After drying the combined organic phases over sodium sulfate and removing the solvent on a rotary evaporator, the residue is purified by means of column chromatography on silica gel (ethyl acetate/saturated methanolic ammonia 95/5). In this way 2.5 g (2S)-l-oxiran-2-ylmethyl-piperidine-4-carboxylic acid ethyl ester is obtained.

$^1$H-NMR (d$^6$-DMSO):δ=4.05 ppm (q, 2H); 3.00 (m, 1H) 2.95 (double-t, 1H); 2.85 (double-t, 1H); 2.70 (q, 1H); 2.62 (dd, 1H); 2.45 (dd, 1H); 2.30 (m, 1H); 2.15 (dd, 1H); 2.02 (m, 2H); 1.75 (broad d, 2H); 1.52 (sextet, 2H); 1.15 (t, 3H).

e) A solution of 0.43 g of the amine produced in c) and 0.173 g of the oxirane produced in d) in 10 ml ethanol is heated for 48 h under reflux. Subsequently the ethanol is removed in a vacuum and the residue is purified by column chromatography on silica gel (ethyl acetate/saturated methanolic ammonia 85/15). The product (325 mg) obtained in this way is taken up in 2 ml dimethylformamide, the solution is admixed with 200 mg carbonyldiimidazole and the reaction mixture is stirred for 15 h at room temperature. Subsequently the reaction mixture is admixed with 10 ml water and it is shaken three times with 10 ml methylene chloride each time. After drying the combined organic phases over sodium sulfate and removing the solvent in a vacuum, the residue is purified by means of preparative HPLC (RP 18, methanol/buffer (pH=7.5) 7/3). In this way 235 mg (1-(5S)-2-oxo-3-(3,4,5,6 -tetrahydro-2H-[1,4']bipyridinyl-4-yl)-oxazolidin-5-ylmethyl]-piperidine-4-carboxylic acid ethyl ester is obtained.

m/e=416; $^1$H-NMR (d$^6$-DMSO) δ=8.12 ppm (d, 2H) 6.82 (d, 2H); 4.60 (q, 1H); 4.05 (q, 2H); 3.99 (broad d, 2H); 3.75 (m, 1H); 3.50 (t, 1H); 3.15 (t, 1H); 2.90 (broad t, 2H); 2.75 (m, 2H); 2.50 (m, 2H); 2.25 (m, 1H); 2.10 (m, 2H); 1.80–1.40 (m, 8H); 1.12 (t, 3H).

f) A solution of 230 mg of the ethyl ester prepared in e) in 2 ml tetrahydrofuran and 1 ml water is admixed with 0.7 ml 1 n sodium hydroxide solution and stirred for 1 h at room temperature. Subsequently the tetrahydrofuran is removed in a vacuum and the product is purified by means of an ion exchanger (Dowex 50, H form). 120 mg of the title compound is obtained in this way as a white powder. FAB=388; $^1$H-NMR (d$^6$-DMSO) δ=8.15 ppm (d, 2H); 6.82 (d, 2H); 4.60 (m, 1H); 4.02 (broad d, 2H); 3.75 (m, 1H); 3.50 (t, 1H); 3.15 (dd, 1H); 2.95 (broad d, 2H); 2.80 (m, 2H); 2.52 (m, 2H); 2.10 (m, 3H); 1.80-1.40 (m, 8H).

EXAMPLE 2

1-[(rac]-2-Oxo-3-(3,4,5,6-tetrahydro-2H-[1,4'] bipyridinyl-4-yl)-oxazolidin-5-ylmethyl]-piperidine-4-carboxylic acid a) A mixture of 3.1 g piperidine-4-carboxylic acid ethyl ester, 6.4 ml epichlorohydrin and 0.1 g tetrabutylammonium bromide in 15 ml toluene and 15 ml concentrated sodium hydroxide solution is stirred for 4 h at room temperature and subsequently admixed with 50 ml water. The organic phase is removed, the aqueous phase is shaken three times with 20 ml methylene chloride each time, the combined organic phases are dried over sodium sulfate and the solvent is removed in a vacuum. 2.1 g (rac)-1-oxiran-2-ylmethylpiperidine-4-carboxylic acid ethyl ester is obtained. m/e=213.

b) Analogously to example 1e), 520 mg 1-[(rac]-2-oxo-3-(3,4,5,6-tetrahydro-2H-[1,4']bipyridinyl-4-yl)-oxazolidin-5-ylmethyl]-piperidine-4-carboxylic acid ethyl ester is obtained from 2.1 g epoxide 2a), 2.6 g amine ic) and 0.4 g carbonyldiimidazole. m/e=416.

c) Analogously to example 1f) 190 mg of the title compound is obtained from 520 mg ethyl ester 2b) and 1.5 ml 1 n sodium hydroxide solution. FAB: 388, $^1$H-NMR (d$^6$-DMSO): identical to $^1$H-NMR of compound 1f).

EXAMPLE 3

{1-[(rac)-2-Oxo-3-(3,4,5, 6-tetrahydro-2H-[1,4'] bipyridinyl-4yl)-oxazolidin-5-ylmethyl]-piperidin-4-ylidene}-acetic acid a) Analogously to example 2a), 1.6 g 8-oxiran-2-ylmethyl-1,4-dioxa-8-aza-spiro[4.5]decane is obtained as a yellow oil from 1.43 g 4-piperidone ethylene ketal, 3.1 ml epichlorohydrin and 0.2 g tetrabutylammonium bromide. $^1$H-NMR (d$^6$-DMSO): δ=3.85 ppm (s, 4H); 3.0 (m, 1H) 2.70 (dt, 2H); 2.60 (d, 1H); 2.50 (m, 3H); 2.40 (m, 1H); 2.20 (dd, 1H); 1.60 (t, 4H)

b) Analogously to example 1e), 0.35 g 5-(1,4-dioxa-8-aza-spiro[4.5]dec-8-ylmethyl)-3-(3,4,5,6-tetrahydro-2H-[1,4']bipyridinyl-4-yl)-oxazolidin-2-one is obtained from 1.6 g epoxide 3a), 1.9 g amine 1c) and 0.4 g carbonyldiimidazole. m/e=402; $^1$H-NMR (d$^6$-DMSO) δ=8.15 ppm (d, 2H) 6.82 (d, 2H); 4.60 (m, 1H); 4.0 (broad d, 2H); 3.85 (s, 4H); 3.75 (m, 1H); 3.52 (t, 1H); 3.15 (t, 1H); 2.90 (broad t, 2H); 2.55 (m, 6H); 1.60 (m, 8H).

c) Analogously to example 1b), 1.1 g 1-[2-oxo-3-(3,4,5, 6-tetrahydro-2H-[1,4']bipyridinyl-4-yl)-oxazolidin-5-ylmethyl]-piperidin-4-one is obtained as a grey powder from 1.2 g ketal 3b) and 10 ml 6 n hydrochloric acid. m/e=358; $^1$H-NMR (CDCl$_3$) δ=8.20 ppm (d, 2H) 6.55 (d, 2H); 4.65 (m, 1H); 3.95 (m, 3H); 3.50 (t, 1H); 3.20 (t, 1H); 2.85 (m, 7H); 2.65 (dd, 1H); 2.45 (t, 4H); 1.80 (m, 2H); 1.65 (dq, 2H).

d) A mixture of 840 mg of the ketone 3c) and 820 mg ethoxycarbonylethylidenetriphenylphosphorane (Aldrid GmbH & Co) in 15 ml toluene is heated for 24 h at 100° C. Subsequently the toluene is evaporated in a vacuum and the crude product is purified on silica gel (ethyl acetate/saturated methanolic ammonia 85/15). In this way 820 mg {1-[(rac)-2-oxo-3-(3,4,5,6-tetrahydro-2H-[1,4']bipyridinyl-4-yl)-oxazolidin-5-ylmethyl]-piperidin-4-ylidene}-acetic acid ethyl ester. m/e 428.

e) Analogously to example if), 48 mg of the title compound is obtained as a white powder from 210 mg ethyl ester 3d) and 0.6 ml 1 n sodium hydroxide solution. FAB: 400; $^1$H-NMR (d$^6$-DMSO): δ=8.15 ppm (d, 2H); 6.80 (d, 2H); 5.60 (s, 1H); 4.65 (m, 1H); 4.05 (broad d, 2H); 3.75 (m, 1H); 3.60 (t, 1H); 3.20 (t, 1H); 2.88 (m, 4H); 2.55 (m, 6H); 2.20 (m, 2H); 1.65 (m, 4H).

EXAMPLE 4

{1-[2-Oxo-3-(3,4,5,6-tetrahydro-2H-[1,4'] bipyridinyl-4-yl)-oxazolidin-5-ylmethyl]-piperidin-4-yl}-acetic acid a) A solution of 560 mg of compound 3d) in 20 ml methanol is admixed with 50 mg palladium/carbon (10%) and hydrogenated at room temperature and normal pressure until the uptake of hydrogen is completed. Afterwards the catalyst is removed by filtration and the solution is evaporated to dryness. In this way 400 mg (1-[2-oxo-3-(3,4,5,6-tetrahydro-2H-[1,4']bipyridinyl-4-yl)-oxazolidin-5-ylmethyl]-piperidin-4-yl} acetic acid ethyl ester is obtained as a colourless oil. m/e=430.

b) Analogously to example if), 180 mg of the title compound is obtained as a light-grey powder from 400 mg ethyl ester 4a) and 1.1 ml 1 n sodium hydroxide solution. FAB=402; $^1$H-NMR (d$^6$-DMSO) δ=8.15 ppm (d, 2H); 6.80 (d, 2H); 4.60 (m, 1H); 4.05 (broad d, 2H); 3.75 (m, 1H); 3.50 (t, 1H); 3.12 (t, 1H); 2.85 (m, 4H); 2.48 (m, 2H); 2.0 (m, 4H); 1.65 (m, 7H); 1.12 (m, 2H)

EXAMPLE 5

{4-Hydroxy-1-[2-oxo-3-(3,4,5,6-tetrahydro-2H-[1, 4']bipyridinyl-4-yl)-oxazolidin-5-ylmethyl]-piperidin-4-yl}acetic acid a) 0.5 ml diisopropylamine is admixed under nitrogen at −10° C. with 2.3 ml n-butyllithium (1.6 M in n-hexane). Subsequently the mixture is stirred for a further 10 minutes at −10° C., then cooled to −78° C. and 10 ml dry tetrahydrofuran is added thereto. 0.45 ml acetic acid tert butyl ester in 2 ml dry tetrahydrofuran is then added dropwise to the lithium diisopropylamide solution prepared in this manner, the reaction mixture is then allowed to stir for 30 min at −78° C., it is admixed with a solution of 1.1 g ketone 3c) in 10 ml dry tetrahydrofuran, it is stirred for 1 h at −78° C. and subsequently slowly heated to room temperature. Afterwards the reaction mixture is stirred for a further 15 h at room temperature and then admixed with 10 ml saturated ammonium chloride solution. After extracting the aqueous solution three times with 10 methylene chloride each time, drying the combined organic phases over sodium sulfate and removing the solvent on a rotary evaporator, the crude product is purified by means of preparative HPLC (Select B, 12μ, methanol/buffer (pH 7.5) 6/4). 0.85 g {4-Hydroxy-1-[2-oxo-3-(3,4,5,6-tetrahydro-2H-[1,4']bipyridinyl-4-yl)-oxazolidin-5-ylmethyl]-piperidin-4-yl}-acetic acid tert.-butyl ester is obtained as a yellow oil. m/e=474.

b) A solution of 100 mg tert.-butyl ester 5a) in 2 ml trifluoroacetic acid is stirred for 5 h at room temperature. Subsequently the reaction mixture is evaporated to dryness, the residue is taken up in 3 ml water and the product is purified by means of an ion exchanger (Dowex 50, H form). 30 mg of the title compound is thus obtained as a white powder. $^1$H-NMR (d$^6$-DMSO): δ=8.15 ppm (d, 2H); 6.85 (d, 2H); 4.60 (m, 1H); 4.05 (broad d, 2H); 3.75 (m, 1H); 3.52 (t, 1H); 3.15 (t, 1H); 2.92 (t, 2H); 2.48 (m, 6H); 2.25 (s, 2H); 1.60 (m, 8H).

EXAMPLE 6

1-[2-Oxo-3-(3,4,5,6-tetrahydro-2H-[1,4']bipyridinyl-4-yl)-oxazolidin-5-ylmethyl]-piperidine-3-carboxylic acid a) Analogously to example 1e), 550 mg 1-[2-oxo-3-(3,4,5,6-tetrahydro-2H)-[1,4']bipyridinyl-4-yl)-oxazolidin-5-ylmethyl]-piperidine-3-carboxylic acid ethyl ester is obtained as a mixture of diastereomers from 2.7 g 1-oxiran-2-ylmethyl-piperidine-3-carboxylic acid ethyl ester (prepared from epichlorohydrin and piperidine-3-carboxylic acid ethyl ester analogously to example 2a)), 3.2 g amine 1c) and 260 mg carbonyldiimidazole. m/e=416.

b) Analogously to example 1f), 300 mg of the title compound is obtained as a light-grey powder from 550 mg ethyl ester 6a) and 1.5 ml 1 n sodium hydroxide solution. m/e=388; $^1$H-NMR (d$^6$-DMSO): diastereomer mixture δ=8.15 ppm (d, 2H); 6.85 (d, 2H); 4.60 (m, 2H); 4.02 (broad d, 2H); 3.72 (m, 1H); 3.50 (t, 1H); 3.15 (t, 1H); 2.90 (broad t, 3H); 2.65 (m, 1H); 2.50 (m, 2H); 2.30–1.95 (m, 3H); 1.80–1.50 (m, 6H); 1.45–1.20 (m, 2H).

EXAMPLE 7

1-[4-Methyl-2-oxo-3-(3,4,5,6-tetrahydro-2H-[1,4'] bipyridinyl-4-yl)-oxazolidin-5-ylmethyl]-piperidine-4-carboxylic acid a) Analogously to example 1d), 14.7 g 1-(3-methyl-oxiranyl-methyl)-piperidin-4-carboxylic acid ethyl ester is obtained as a yellow oil from 20.3 g (rac)-trans-2-(p-toluenesulfonyloxymethyl)-3-methyloxirane (Evans R. D., Synthesis, p. 862 (1988)), 13.9 ml piperidine-4-carboxylic acid ethyl ester and 13.8 g potassium carbonate in 50 ml dimethylformamide after stirring for 12 hours at room temperature.

$^1$H-NMR (d$^6$-DMSO) δ=4.08 ppm (q, 2H) 2.99 (dt, 1H); 2.90–2.65 (m, 3H); 2.55 (dd, 1H); 2.32–2.12 (m, 2H); 2.10–1.95 (m, 2H); 1.90–1.62 (m, 4H); 1.21 (d, 3H); 1.18 (t, 3H).

b) A solution of 2.5 g of the epoxide prepared in 7a), 1.0 g sodium azide and 0.810 g ammonium chloride is heated for 24 h at 50° C. in 25 ml of an ethanol/water (80/20) mixture. Subsequently the ethanol is removed in a vacuum, the residue is diluted with 10 ml water and the aqueous solution is extracted three times with 15 ml methylene chloride each time. After drying the combined organic phases over sodium sulfate and removing the solvent on a rotary evaporator, the crude product is chromatographed on silica gel (ethyl acetate/isohexane: 3/1). 1.4 g 1-(3-azido-2-hydroxy-butyl)-piperidine-4-carboxylic acid ethyl ester is obtained in this way.

$^1$H-NMR (CDCl$_3$): δ=4.05 ppm (q, 2H); 3.48 (m, 1H) 2.40 (m, 1H); 2.77–2.57 (m, 2H); 2.48 (d, 1H); 2.35–2.08 (m, 4H); 2.02–1.55 (m, 5H); 1.20 (d and t, 5H).

c) A solution of 1.4 g of the azide prepared in 7b) in 20 ml ethanol is admixed with 0.5 g 10% palladium/carbon and the mixture is hydrogenated for 8 h at room temperature. Afterwards the catalyst is removed by filtration and the solution is concentrated on a rotary evaporator. 1.1 g 1-(3-amino-2-hydroxy-butyl)-piperidine-4-carboxylic acid ethyl ester is obtained in this way.

d) A solution of 1.0 g amine 7c), 0.721 g ketone 1b) and 1.1 g sodium triacetateborohydride in 15 ml methylene chloride is stirred for 15 h at room temperature. Subsequently the reaction mixture is admixed with 10 ml water and acidified with 1 N hydrochloric acid. After separating the phases the aqueous acidic phase is again extracted with 10 ml methylene chloride and then made alkaline with 1 N sodium hydroxide solution. After extracting the alkaline mixture three times with 15 ml methylene chloride each time and drying the combined organic phases over sodium sulfate, the solvent is removed on a rotary evaporator. The crude product is then purified by means of preparative HPLC (RP 18, methanol/buffer (pH=7.75) 70/30). In this way 0.5 g 1-[2-hydroxy-3-(3,4,5,6-tetrahydro-2H-[1,4'] bipyridinyl-4-ylamino)-butyl]-piperidine-4-carboxylic acid ethyl ester is obtained.

$^1$H-NMR (CDCl$_3$): δ=8.15 ppm (d, 2H); 6.60 (d, 2H) 4.05 (q, 2H); 3.78 (t, 1H); 3.72 (t, 1H); 3.58 (m, 1H); 2.97–2.70 (m, 5H); 2.40–2.25 (m, 4H); 2.06–1.60 (m, 7H); 1.38–1.10 (m, 3H); 2.20 (t, 3H); 0.98 (d, 3H).

e) A solution of 0.5 g of the aminoalcohol 7d) and 243 mg carbonyldiimidazole in 5 ml dimethyl-formamide is stirred for 24 h at room temperature. Subsequently the reaction solution is evaporated to dryness and the residue is purified by means of preparative HPLC (Merck, Select B, methanol/buffer (pH=7.5) 65/35). 0.26 g 1-[4-methyl-2-oxo-3-(3,4,5, 6-tetrahydro-2H-[1,4']bipyridinyl-4-yl)-oxazolidin-5-ylmethyl]-piperidine-4-carboxylic acid ethyl ester is obtained in this way. m/e=430 f) A solution of 0.26 g of the ethyl ester 7e) and 0.72 ml 1 N sodium hydroxide solution in 5 ml methanol is stirred for 1 h at room temperature. Subsequently the methanol is removed in a vacuum and the product is purified by means of an ion exchanger (Dowex 50, H form). In this way 0.11 g of the title compound is obtained as a white powder. f.p.>220° C. FAB=402. ¹H-NMR (d⁶-DMSO): δ=8.15 ppm (d, 2H); 6.80 (d, 2H); 4.55 (q, 1H); 3.98 (m, 3H); 3.55 (, 1H); 2.82 (m, 4H); 2.50 (m, 8 lines, 1H); 2.0 (m, 4H); 1.75 (m, 6H); 1.50 (broad q, 2H); 1.09 (d, 3H)

EXAMPLE 8

1-[2-Oxo-3-(1-pyrimidin-4-yl-piperidin-4-yl)-oxazolidin-5-ylmethyl]-piperidine-4-carboxylic acid a) A solution of 18.5 g 2,4-dichloropyrimidine in 150 ml ethanol is added dropwise to a solution of 16 ml 4-piperidone-ethylene ketal and 17.5 ml triethylamine in 100 ml ethanol while cooling on ice. Subsequently the reaction mixture is stirred for a further 2.5 hours, the ethanol is then removed in a vacuum, the residue is admixed with 100 ml water and the aqueous mixture is extracted three times with 50 ml methylene chloride each time. After drying the combined organic phases over sodium sulfate and removing the solvent, the solid residue is recrystallized from ethyl acetate/isohexane. In this way 11 g 8-(2-chloro-pyrimidin-4-yl)-1,4-dioxa-8-aza-spiro[4.5]decane is obtained as a white powder. f.p.: 135–137° C.

b) 6 g of the 2-chloropyrimidine 8a) is dissolved in 60 ml methanol and 20 ml tetrahydrofuran and hydrogenated for 6 hours at room temperature and 44 mbar after the addition of 4.2 g potassium carbonate and 1 g 10% palladium/carbon. Subsequently the reaction mixture is filtered, the filtrate is evaporated to dryness, the residue is taken up in 20 ml water and the aqueous mixture is extracted three times with 20 ml methylene chloride each time. After drying the combined organic phases over sodium sulfate and removing the solvent 4.9 g 8-pyrimidin-4-yl-1,4-dioxa-8-aza-spiro[4.5]decane is obtained as a white powder. m/e: 221 c) Analogously to example 1b), 3.9 g 1-pyrimidin-4-yl-piperidin-4-one is obtained as a yellow powder from 4.9 g ketal 8b) and 60 ml 6 N hydrochloric acid in 60 ml tetrahydrofuran after a reaction time of 55 hours. f.p.: 75–80° C.

d) 8.5 g crude product is obtained analogously to example 7b) from 8 g epoxide 2a), 3.8 g sodium azide and 3.2 g ammonium chloride in 100 ml methanol/water (8/1), the purification of which by means of column chromatography on silica gel (ethyl acetate/0.1% methanolic ammonia) yields 7.4 g (77%) 1-(3-azido-2-hydroxy-propyl-)piperidine-4-carboxylic acid ethyl ester as a yellow oil.

¹H-NMR (d⁶-DMSO): δ=5.01 ppm (broad s, 1H; OH); 4.05 (q, 2H); 3.80 (m, 1H); 3.20 (dddd, 2H); 2.85 (m, 2H); 2.30 (m, 3H); 2.05 (q, 2H); 1.88 (broad d, 2H); 1.55 (m, 2H); 1.12 (t, 3H).

e) Analogously to example 7c), 2.9 g 1-(3-amino-2-hydroxy-propyl)-piperidine-4-carboxylic acid ethyl ester is obtained as a viscous yellow oil after hydrogenating 3.6 g azide 8d).

f) Analogously to example 7d), 1 g 1-[2-hydroxy-3-(1-pyrimidin-4-yl-piperidin-4-ylamino)-propyl]-piperidine-4-carboxylic acid ethyl ester is obtained as a light-yellow oil from 2.5 g amine 8e), 1.9 g ketone 8c) and 4.6 g sodium triacetate borohydride. ¹H-NMR (d⁶-DMSO): δ=8.49 ppm (s, 1H); 8.15 (d, 1H); 6.80 (d, 1H); 4.21 (broad d, 2H); 4.05 (q, 2H); 3.61 (m, 1H); 3.02 (t, 2H); 2.80 (m, 1H); 2.65 (m, 2H); 2.45 (m, 1H); 2.24 (m, 3H); 2.00 (t, 3H); 1.88–1.68 (m, 4H); 1.57 (m, 2H); 1.25 (t, 3H); 1.19 (m, 3H).

g) Analogously to example 7e), the reaction of 1 g aminoalcohol 8f) and 0.83 g 1.1'-carbonyldiimidazole in 10 ml dimethylformamide yields 1.2 g 1-[2-oxo-3-(1-pyrimidin-4-yl-piperidin-4-yl)-oxazolidin-5-ylmethyl]-piperidine-4-carboxylic acid ethyl ester as a yellow oil. FAB (MH⁺): 418.

h) Analogously to example 7f), the saponification of 1.1 g ethyl ester 8g) yields 0.61 g of the title compound as a white powder. f.p.: 145° C. FAB (MH⁺): 418. ¹H-NMR (d⁶-DMSO): 6 8.22 ppm (s, 1H); 7.90 (d, 1H); 6.60 (d, 1H); 4.40 (m, 1H); 4.30 (m, 2H); 3.58 (m, 1H); 3.31 (t, 1H); 2.92 (m, 1H); 2.70 (t, 3H); 2.25 (m, 3H); 1.81 (m, 3H); 1.50 (m, 4H) 1.32 (m, 4H).

EXAMPLE 9

1-{3-[1-(2-Benzylamino-pyrimidin-4-yl)-piperidin-4-yl]-2-oxo-oxazolidin-5-ylmethyl}-piperidine-4-carboxylic acid a) A mixture of 8 g 8-(2-chloro-pyrimidin-4-yl)-1,4-dioxa-8-aza-spiro[4.5]decane 8a) and 7.2 ml benzylamine is heated for 2 hours at 150° C., then cooled, admixed with 20 ml water and the aqueous solution is extracted three times with 20 ml methylene chloride each time. After drying the combined organic phases over sodium sulfate and removing the solvent, the residue is washed with cold isohexane. In this way 9.6 g benzyl-[4-(1,4-dioxa-8-aza-spiro[4.5]dec-8-yl)-pyrimidin-2-yl]amine is obtained as a yellow powder. ¹H-NMR (d⁶-DMSO): δ=7.85 ppm (d, 1H); 7.40–7.18 (m, 5H) 7.15 (broad s, 1H, NH); 6.12 (d, 1H); 4.45 (d, 2H); 3.96 (s, 4H); 3.65 (m, 4H); 1.61 (m, 4H).

b) Analogously to example 1b), 10.29 g 1-(2-benzyl-amino-pyrimidin-4-yl)-piperidin-4-one is obtained as a brown powder after a reaction time of 20 hours from 9.6 g ketal 9a) and 85 ml 6 N hydrochloric acid in 80 ml tetrahydrofuran. f.p.: 98–102° C.

c) Analogously to example 7d), 3.4 g 1-{3-[1-(2-benzylamino-pyrimidin-4-yl)-piperidin-4-ylamino]-2-hydroxy-propyl}-piperidine-4-carboxylic acid ethyl ester is obtained as a yellow oil from 3.1 g ketone 9b), 2.5 g amine 8e) and 4.6 g sodium triacetate-borohydride. m/e=496. ¹H-NMR (d⁶-DMSO): δ=7.52 ppm (d, 1H); 7.10–6.95 (m, 5H); 6.80 (broad s, 1H, NH): 5.80 (d, 1H); 4.15 (d, 2H); 3.90 (m, 2H); 3.80 (q, 2H); 3.39 (m, 1H); 3.05 (broad s, 1H); 2.75–2.52 (m, 3H); 2.40 (m, 1H); 2.25 (m, 1H); 2.05 (m, 2H); 1.75 (m, 1H); 1.55 (m, 4H); 1.32 (m, 2H); 0.95 (t, 3H); 0.88 (m, 5H).

d) Analogously to example 7e), the reaction of 3.4 g aminoalcohol 9c) and 2.2 g 1,1'-carbonyldiimidazole in 20 ml dimethylformamide yields 2.3 g 1-{3-[1-(2-benzylamino-pyrimidin-4-yl)-piperidin-4-yl]-2-oxo-oxazolidin-5-ylmethyl}-piperidine-4-carboxylic acid ethyl ester as a yellow powder. f.p.: 122° C.

e) Analogously to example 7f), the saponification of 0.26 g ethyl ester 9d) yields 0.21 g of the title compound as a white powder. f.p.: 125–130° C. FAB (MH⁺) : 495. ¹H-NMR (d⁶-DMSO) : δ=7.90 ppm (d, 1H); 7.39 (d, 2H); 7.24 (m, 3H); 6.12 (d, 1H); 4.68 (q, 1H); 4.51 (d, 2H); 4.45 (m, 2H); 3.85 (t, 1H); 3.55 (t, 1H); 3.20 (t, 1H); 2.85 (m, 3H); 2.55 (m, 3H); 2.18 (m, 3H); 1.75 (m, 3H); 1.50 (m, 3H).

EXAMPLE 10

The following compounds were produced in an analogous manner:
a) 1-[2-Oxo-4-phenyl-3-(3,4,5,6-tetrahydro-2H-[1,4']bipyridinyl-4-yl)-oxazolidin-5-ylmethyl]-piperidine-4-carboxylic acid; f.p. 150° C. (decomp.); m/e=464
b) 1-[2-Oxo-4-phenyl-3-(3,4,5,6-tetrahydro-2H-[1,4']bipyridinyl-4-yl)-oxazolidin-5-carbonyl]-piperidine-carboxylic acid; f.p. 77–80° C.; m/e=478 c) 4-Hydroxy-4-[2-oxo-3-(3,4,5,6-tetrahydro-2H-[1,4']bipyridinyl-4-yl)-oxazolidin-5-ylmethyl]-cyclohexanecarboxylic acid; f.p.>250° C.; m/e=403 d) 1-[4-(4-Methoxy-phenyl)-2-oxo-3-(3,4,5,6-tetrahydro-2H-[1,4']bipyridinyl-4-yl)-oxazolidin-5-carbonyl]-piperidine-4-carboxylic acid; f.p. 199° C. decomp.); m/e=508

EXAMPLE 11

1-[2-Oxo-3-(3,4,5,6-tetrahydro-2H-[1,4']bipyridinyl-4-ylmethyl)-oxazolidin-5-ylmethyl]-piperidine-4-carboxylic acid a) A mixture of 4.4 g (39 mmol) 4-chloropyridine and 4.4 g (39 mmol) 4-aminomethylpiperidine is stirred for 1 hour at 150° C. oil-bath temperature. Subsequently the melt is taken up in water, washed with ether, the aqueous phase is made alkaline with 10 N sodium hydroxide solution and it is extracted using dichloromethane. After drying the extract over sodium sulfate and removing the solvent, 4.4 g (59% of theory) 3,4,5,6-tetrahydro-2H-[1,4']bipyridinyl-4-ylmethylamine remains as a viscous oil. m/e=191; $^1$H-NMR (CDCl$_3$) : δ=8.25 ppm (d, 2H); 6.70 (d, 2H); 3.90 (d with fine resolution, 2H); 2.85 (t with fine resolution, 2H); 2.60 (d, 2H); 1.80 (m, 4H); 1.55 (m, 1H); 1.25 (q with fine resolution, 2H).

b) Analogously to example 1e) 1.0 g 1-[2-oxo-3-(3,4,5,6-tetrahydro-2H-[1,4']bipyridinyl-4-ylmethyl)-oxazolidin-5-ylmethyl]-piperidine-4-carboxylic acid ethyl ester is obtained from 2.8 g epoxide 2a), 2.6 g amine 11a) and 0.5 g carbonyldiimidazole. m/e=404; $^1$H-NMR (CDCl$_3$) δ=8.20 ppm (d, 2H); 6.65 (d, 2H); 4.65 (q, 1H); 4.10 (q, 2H); 3.90 (broad d, 2H); 3.65 (m, 1H); 3.50 (s, 1H); 3.35 (t, 1H); 3.15 (d, 2H); 2.85 (m, 4H); 2.60 (d, 1H); 2.50 (m, 1H); 2.25 (m, 2H); 1.80 (m, 8H); 1.25 (t+m, 5H).

c) Analogously to example 1f) 1.5 g of the title compound is obtained from 3.0 g ethyl ester 1ib) and 12 ml 1 N sodium hydroxide solution as a white powder with a melting point of 94–96° C. m/e=402; $^1$H-NMR (d$_6$-DMSO) : δ=8.10 ppm (d, 2H); 6.85 (d, 2H); 4.60 (m, 1H); 3.95 (broad d, 2H); 3.25 (dd, 1H); 3.05 (d, 2H); 2.85 (m, 4H); 2.15 (m, 3H); 1.75 (m, 8H); 1.15 (m, 4H)

EXAMPLE 12

1-{2-Oxo-3-[2-(3,4,5,6-tetrahydro-2H-[1.4']bipyridinyl-4-yl)-ethyl]-oxazolidin-5-ylmethyl}-piperidine-4-carboxylic acid a) Analogously to example 11a) 5.2 g (51% of theory) 2-(3,4,5,6-tetrahydro-2H-[1,4']bipyridinyl-4-yl)-ethylamine is obtained from 5.7 g 4-chloropyridine and 12.8 g 4-(2-amino-ethyl)piperidine (boiling point$_{21}$ 100–104° C.; prepared by hydrogenating 4-(2-amino-ethyl)pyridine [J. Amer. Chem. Soc. 78, 4129 (1956)] over ruthenium at 150° C. and 150 bar hydrogen pressure). m/e=205; $^1$H-NMR (CDCl$_3$) δ=8.20 ppm (d, 2H); 6.65 (d, 2H); 3.80 (broad d, 2H) 2.75 (m, 4H); 1.80–1.10 (m, 9H).

b) Analogously to example 1e) 0.8 g 1-{2-oxo-3-[2-(3,4,5,6-tetrahydro-2H-[1,4']bipyridinyl-4-yl)-ethyl]-oxazolidin-5-ylmethyl}-piperidine-4-carboxylic acid ethyl ester is obtained from 1.9 g epoxide 2a), 5.1 g amine 12a) and 0.5 g carbonyldiimidazole. m/e=444.

c) Analogously to example 1f) 0.4 g of the title compound is obtained as an amorphous powder from 0.7 g ethyl ester 12b) and 5 ml 1 N sodium hydroxide solution. m/e=416; $^1$H-NMR (CDCl$_3$) δ=8.15 ppm (d, 2H); 6.65 (d, 2H); 4.60 (m, 1H); 3.80 (broad d, 2H); 3.55 (t, 1H); 3.25 (m, 2H); 2.80 (m, 6H); 2.55 (br, 1H); 2.15 (m, 2H); 1.90–0.80 (m, 13H).

EXAMPLE 13

1-{2-Oxo-3-[1-(2-pyridin-4-yl-ethyl)-piperidin-4-yl]-oxazolidin-5-ylmethyl}-piperidine-4-carboxylic acid a) Analogously to example 7b) 29 g (94% of theory) 1-(3-azido-2-hydroxy-propyl)piperidine-4-carboxylic acid ethyl ester is obtained as an oil from 25.6 g epoxide 2a) and 39 g sodium azide. m/e=256 b) Analogously to example 7c) 21.1 g (81% of theory) 1-(3-amino-2-hydroxy-propyl)piperidine-4-carboxylic acid ethyl ester is obtained by catalytic reduction from 29 g azide 13a). m/e=230; $^1$H-NMR (CDCl$_3$) δ=4.15 ppm (q, 2H); 3.65 (m, 1H); 2.95 (m, 1H); 2.80 (dd, 2H); 2.65 (dd, 1H); 2.30 (m, 7H); 2.05–1.65 (m, 4H); 1.25 (t, 3H).

c) A solution of 16.2 ml (150 mmol) 4-vinylpyridine in 5.7 ml glacial acetic acid is admixed with 12.8 ml 4-piperidone-ethylene ketal and heated for 3 hours to 100° C. Subsequently the reaction mixture is made alkaline with 2 N sodium hydroxide solution, stirred for 15 min at room temperature and then admixed with 10 N sodium hydroxide solution in order to separate the base. It is extracted with dichloromethane, dried over sodium sulfate, evaporated in a vacuum and chromatographed on silica gel. 16.3 g (66% of theory) 8-(2-pyridin-4-yl-ethyl)-1,4-dioxa-8-aza-spiro[4,5]decane is eluted using isohexane/ethyl acetate 3:1. $^1$H-NMR (CDCl$_3$): δ=8.50 ppm (d, 2H); 7.15 (d, 2H); 3.95 (s, 4H), 2.75 (m, 2H); 2.55 (m, 6H); 1.75 (dd, 4H).

d) Analogously to example 1b) 10.2 g (100% of theory) 1-(2-pyridin-4-yl-ethyl)-piperidin-4-one is obtained as an oil from 12.4 g ketal 13c). $^1$H-NMR (CDCl$_3$) : δ=8.50 ppm (d, 2H); 7.15 (d, 2H); 2.75 (m, 8H); 2.45 (t, 4H).

e) Analogously to example 7d) 0.9 g 1-{2-hydroxy-3-[1-(2-pyridin-4-yl-ethyl)piperidin-4-ylamino]propyl}-piperidine-4-carboxylic acid ethyl ester is obtained as an oil from 2.1 g amine 13b) and 1.9 g ketone 13d). $^1$H-NMR (CDCl$_3$): δ=8.50 ppm (d, 2H); 7.15 (d, 2H); 4.10 (q, 2H); 3.80 (m, 1H); 2.90 (m, 4H); 2.75 (m, 4H); 2.55 (m, 4H); 2.30 (m, 4H); 2.05 (m, 2H); 1.85 (br, d, 4H); 1.75 (m, 2H); 1.40 (m, 2H); 1.25 (t, 3H).

f) Analogously to example 7e) 1.7 g 1-{2-oxo-3-[1-(2-pyridin-4-yl-ethyl)-piperidin-4-yl]-oxazolidin-5-ylmethyl}-piperidine-4-carboxylic acid ethyl ester is obtained as an oil from 2.6 g of the aminoalcohol 13e) and 1.3 g carbonyldiimidazole. m/e=444; $^1$H-NMR (CDCl$_3$): δ=850 ppm (d, 2H); 7.15 (d, 2H); 4.60 (m, 1H); 4.15 (q, 2H); 3.70 (m, 1H); 3.55 (t, 1H); 3.30 (t, 1H); 3.05 (br, d, 2H); 2.80 (m, 4H); 2.60 (m, 4H); 2.20 (m, 5H); 1.80 (m, 8H); 1.25 (t, 3H).

g) Analogously to example 1f) 1.2 g (75% of theory) of the title compound is obtained as an amorphous powder from 1.7 g ethyl ester 13f) and 5.2 g 1 N sodium hydroxide solution. m/e=416; $^1$H-NMR (d$_6$-DMSO): δ=8.20 ppm (d, 2H); 7.05 (d, 2H); 4.40 (br, t, 1H); 3.30 (m, 2H); 2.95 (t, 1H); 2.75 (br, d, 2H); 2.55 (m, 4H); 2.25 (m, 4H); 1.80 (m, 5H); 1.55 (m, 2H); 1.35 (m, 6H).

EXAMPLE 14

Pharmacological data

Assay

Microtitre plates were coated overnight with 2 μg/ml isolated activated GpIIb/IIIa receptor. After the unbound receptor had been removed by several washing steps, the surface of the plate was blocked with 1% casein and washed again. The test substance was added at the necessary concentrations, the plates were subsequently incubated for 10 minutes while shaking in a linear shaker. The natural ligand of the GpIIb/IIIa receptor fibrinogen was added thereto. After incubating for 1 hour, unbound fibrinogen was removed by several washing steps and bound fibrinogen was determined in an ELISA reader by determining the change in optical density at 405 nm caused by a peroxidase conjugated monoclonal antibody. Inhibition of the fibrinogen-GpIIb/IIIa interaction leads to low optical densities. The $IC_{50}$ value was determined by means of a concentration-effect curve.

Literature:

The GpIIb/IIIa fibrinogen ELISA is a modification of the assay which is described in the following references:

Nachman, R. L. & Leung, L. L. K. (1982): Complex formation of platelet membrane glycoproteins IIb and IIIa with fibrinogen. J. Clin. Invest. 69: 263–269.

Wright, P. S. et al. (1983); An echistatin C-terminal peptide activated GpIIb/IIIa binding to fibrinogen, fibronectin, vitronectin and collagen type I and type IV. Biochem. J. 293: 262–267.

TABLE

| Example | $IC_{50}$ (μmol/l) | Name |
|---|---|---|
| 1 | <0.30 | 1-[(5S)-2-oxo-3-(3,4,5,6-tetrahydro-2H-[1,4']bipyridinyl-4-yl)-oxazolidin-5-ylmethyl]-piperidine-4-carboxylic acid |
| 2 | <0.30 | 1-[(rac)-2-oxo-3-(3,4,5,6-tetrahydro-2H-[1,4']bipyridinyl-4-yl)-oxazolidin-5-ylmethyl]-piperidine-4-carboxylic acid |
| 3 | 1.40 | {1-[(rac)-2-oxo-3-(3,4,5,6-tetrahydro-2H-[1,4']bipyridinyl-4-yl)-oxazolidin-5-ylmethyl]-piperidin-4-ylidene}-acetic acid |
| 5 | 1.00 | {4-hydroxy-1-[2-oxo-3-(3,4,5,6-tetrahydro-2H-[1,4']bipyridinyl-4-yl)-oxazolidin-5-ylmethyl]-piperidin-4-yl}-acetic acid |
| 7 | <0.30 | 1-[4-methyl-2-oxo-3-(3,4,5,6-tetrahydro-2H-[1,4']bipyridinyl-4-yl)-oxazolidin-5-ylmethyl]-piperidine-4-carboxylic acid |
| 8 | 0.30 | 1-[2-oxo-3-(1-pyrimidin-4-yl-piperidin-4-yl)-oxazolidin-5-ylmethyl]-piperidine-4-carboxylic acid |
| 9 | 0.070 | 1-{3-[1-(2-benzylamino-pyrimidin-4-yl)-piperidin-4-yl]-2-oxo-oxazolidin-5-ylmethyl}-piperidine-4-carboxylic acid |
| 10 a) | 0.30 | 1-[2-oxo-4-phenyl-3-(3,4,5,6-tetrahydro-2H-[1,4']bipyridinyl-4-yl)-oxazolidin-5-ylmethyl]-piperidine-4-carboxylic acid |
| 10 c) | <0.30 | 4-hydroxy-4-[2-oxo-3-(3,4,5,6-tetrahydro-2H-[1,4']bipyridinyl-4-yl)-oxazolidin-5-ylmethyl]-cyclohexanecarboxylic acid |
| No. 78 | 0.60 | (5S)-1-[5-methyl-2-oxo-3-(3,4,5,6-tetrahydro-2H-[1,4']bipyridinyl-4-yl)-oxazolidin-5-ylmethyl]-piperidine-4-carboxylic acid |
| No. 79 | 1.30 | 1-[2-oxo-3-(3,4,5,6-tetrahydro-2H-[1,4']-bipyridinyl-4-yl)-4-(3-trifluoromethyl-phenyl)-oxazolidin-5-ylmethyl]-piperidine-4-carboxylic acid |
| No. 80 | 0.50 | 1-[4-(4-chloro-phenyl)-2-oxo-3-(3,4,5,6-tetrahydro-2H-[1,4']bipyridinyl-4-yl)-oxazolidin-5-ylmethyl]-piperidine-4-carboxylic acid |

We claim:
1. A compound of formula I,

(I)

wherein
X, Y and Q are independently selected from the group consisting of nitrogen and CH;
W is selected from the group consisting of hydrogen and —$NR^{0}R^{00}$;
Z is selected from the group consisting of nitrogen, CH and C—OH;
A, E, and G are independently selected from the group consisting of a valency bond and an alkylene chain —$(CH_2)_n$—;
B is a valency bond or when Z is nitrogen, B is a carbonyl group;
D is a side chain of the formula —$(CHR^3)_m$—COO— or =$CR^3$—COO—;
n is 1–5;
m is 0 or 1;
$R^1$ and $R^2$ are independently selected from the group consisting of hydrogen, $C_{1-6}$ alkyl, and aryl or $R^1$ and $R^2$ together form a carbocyclic five-membered or six-membered ring,
$R^3$ is selected from the group consisting of hydrogen, —$OR^5$ and —$NR^6R^7$;
$R^4$ is selected from the group consisting of hydrogen and —$OR^5$;
$R^5$ is selected from the group consisting of hydrogen, $C_{1-6}$alkyl, aryl and aryl$C_{1-6}$alkyl;
$R^6$ is selected from the group consisting of hydrogen, $C_{1-6}$ alkyl and aryl$C_{1-6}$alkyl;
$R^7$ is selected from the group consisting of hydrogen, $C_{1-6}$ alkyl, aryl$C_{1-6}$alkyl, acyl, $C_{1-4}$alkylsulfonyl and arylsulfonyl;
$R^0$ and $R^{00}$ are independently selected from the group consisting of hydrogen, $C_{1-6}$ alkyl, aryl, aryl$C_{1-6}$alkyl, hetaryl, acyl and a carbocyclic or heterocyclic ring which is unsubstituted or substituted at least once with a $C_{1-6}$ alkyl, or $R^0$ and $R^{00}$ together with the nitrogen to which they are bound form a five-membered or six-membered ring which is unsubstituted or substituted at least once with a $C_{1-6}$ alkyl,
as well as conformational isomers and pharmacologically acceptable salts thereof.

2. The compound according to claim 1, wherein $R^0$ and $R^{00}$ together with the nitrogen to which they are bound form a five-membered or six-membered ring which is unsubstituted or substituted at least once with a $C_{1-6}$ alkyl and contains 1–3 additional heteroatoms.

3. The compound according to claim 1, wherein n is selected from the group consisting of 1, 2 and 3.

4. The compound according to claim 1, wherein each aryl is a phenyl residue.

5. The compound according to claim 1, wherein each acyl is independently selected from the group consisting of formyl, acetyl, propionyl, butyryl and benzoyl residues.

6. The compound according to claim 1, wherein arylsulfonyl is selected from the group consisting of benzene sulfonic acid and toluene sulfonic acid.

7. A compound according to claim 1, wherein said compound is selected from the group consisting of 1-[(5S)-2-oxo-3-(3,4,5,6-tetrahydro-2H-[1, 4']bipyridinyl-4-yl)-oxazolidin-5-ylmethyl]piperidine-4-carboxylic acid 1-[(rac)-2-oxo-3-(3,4,5,6-tetrahydro-2H-[1,4'] bipyridinyl-4-yl)-oxazolidin-5-ylmethyl]-piperidine-4-carboxylic acid {1-[(rac)-2-oxo-3-(3,4,5,6-tetrahydro-2H-[1, 4']bipyridinyl 4-yl)-oxazolidin-5-ylmethyl]-piperidin-4-ylidene}-acetic acid {4-hydroxy-1-[2-oxo-3-(3,4,5,6-tetrahydro-2H-[1,4'] bipyridinyl-4-yl)-oxazolidin-5-ylmethyl]-piperidin-4-yl}-acetic acid 1-[4-methyl-2-oxo-3-(3,4,5,6-tetrahydro-2H-[1,4'] bipyridinyl-4-yl)-oxazolidin-5-ylmethyl]-piperidine-4-carboxylic acid 1-[2-oxo-4-phenyl-3-(3,4,5,6-tetrahydro-2H-[1, 4']bipyridinyl-4-yl)-oxazolidin-5-ylmethyl]-piperidine-4-carboxylic acid 1-[2-oxo-3-(1-pyrimidine-4-yl-piperidine-4-yl) oxazolidin-5-ylmethyl]-piperidine-4-carboxylic acid 1-{3-[1-(2-benzylamino-pyrimidine-4-yl)-piperidine-4-yl]-2-oxo-oxazolidin-5 -ylmethyl}-piperidin-4-carboxylic acid 4-hydroxy-4-[2-oxo-3-(3,4,5,6-tetrahydro-2H-[1, 4']bipyridinyl 4-yl)-oxazolidin-5-ylmethyl]-cyclohexanecarboxylic acid (5S)-1-[5-methyl-2-oxo-3-(3,4,5,6-tetrahydro-2H-[1,4'] bipyridinyl-4-yl) -oxazolidin-5-ylmethyl]-piperidine-4-carboxylic acid 1-[2-oxo-3-(3,4,5,6-tetrahydro-2H-[1,4']bipyridinyl-4-yl)-4-(3-trifluoromethylphenyl)-oxazolidin-5-ylmethyl]-piperidine-4-carboxylic acid, and 1-[4-(4-chloro-phenyl)-2-oxo-3-(3,4,5,6-tetrahydro-2H-[1,4']bipyridinyl-4-yl)-oxazolidin-5-ylmethyl]-piperidine-4-carboxylic acid and the conformational isomers and pharmacologically acceptable salts thereof.

8. A pharmaceutical composition for inhibiting the aggregation of blood platelets, comprising an aggregation inhibiting amount of at least one compound according to claim 6 in combination with a pharmaceutically acceptable carrier.

9. A method for inhibiting blood platelet aggregation, comprising administering an amount of a compound according to claim 1 effective to inhibit blood platelet aggregation to a patient in need of such treatment.

10. A method for treating a condition caused by a thromboembolic occurrence resulting from blood platelet aggregation, comprising administering an amount of a compound according to claim 1 effective to inhibit blood platelet aggregation to a patient in need of such treatment.

11. The method according to claim 10, wherein said condition caused by a thromboembolic occurrence is selected from the group consisting of stroke, myocardial infarction and arterial occlusion.

* * * * *